(12) United States Patent
Morimoto et al.

(10) Patent No.: US 7,169,873 B2
(45) Date of Patent: Jan. 30, 2007

(54) SILSESQUIOXANE DERIVATIVES AND PROCESS FOR PRODUCTION THEREOF

(75) Inventors: Yoshitaka Morimoto, Kanagawa (JP); Kenichi Watanabe, Kanagawa (JP); Nobumasa Ootake, Kanagawa (JP); Jyun-ichi Inagaki, Kanagawa (JP); Kazuhiro Yoshida, Kanagawa (JP); Koji Ohguma, Kanagawa (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 10/490,163

(22) PCT Filed: Sep. 17, 2002

(86) PCT No.: PCT/JP02/09538

§ 371 (c)(1), (2), (4) Date: Apr. 30, 2004

(87) PCT Pub. No.: WO03/024870

PCT Pub. Date: Mar. 27, 2003

(65) Prior Publication Data

US 2004/0249103 A1 Dec. 9, 2004

(30) Foreign Application Priority Data

Sep. 18, 2001 (JP) .............................. 2001-283304
Sep. 3, 2002 (JP) .............................. 2002-257738

(51) Int. Cl.
*C07F 7/21* (2006.01)

(52) U.S. Cl. .............................. 528/37; 528/36; 528/30; 528/32; 556/460; 556/417; 556/429; 556/438; 556/451; 556/455; 556/452

(58) Field of Classification Search ................ 528/37, 528/32, 30, 36; 556/450, 417, 429, 438, 556/451, 445, 452

See application file for complete search history.

(56) References Cited

U.S. PATENT DOCUMENTS 4,528,390 A * 7/1985 Kimura ...................... 556/450
5,973,095 A * 10/1999 Hacker et al. ................ 528/12
6,660,823 B1 * 12/2003 Lichtenhan et al. .......... 528/37

FOREIGN PATENT DOCUMENTS

| EP | 348705 | 1/1990 |
|----|--------|--------|
| EP | 624591 | 11/1994 |
| JP | 2000-334881 | 12/2000 |
| JP | 2001-48890 | 2/2001 |

* cited by examiner

*Primary Examiner*—Margaret G. Moore
(74) *Attorney, Agent, or Firm*—Wenderoth, Lind & Ponack, L.L.P.

(57) ABSTRACT

The present inventors have obtained a PSQ derivative of a completely condensed type into which a functional group is readily introduced by using a novel PSQ derivative of an incompletely condensed type in which four alkaline metal atoms are bonded to silsesquioxane of a cage type having eight Si's. The above silsesquioxane derivative is represented by Formula (1). A silsesquioxane derivative to which alkaline metal atoms are bonded is represented by Formula (2). In Formula (1) and Formula (2), R is a group selected from alkyl, aryl and arylalkyl; Y is a group represented by Formula (a) or Formula (b); and M is a monovalent alkaline metal atom. X in Formula (a) and Formula (b) is hydrogen, halogen, a hydroxyl group or a monovalent organic group, and Z is —O—, —$CH_2$— or a single bond. The preferred organic group is a functional group or a group having a functional group.

23 Claims, No Drawings

SILSESQUIOXANE DERIVATIVES AND PROCESS FOR PRODUCTION THEREOF

FIELD OF THE INVENTION

The present invention relates to a silsesquioxane derivative used as an electronic material, an optical material an electronic-optical material or a catalyst carrier and a production process for the same. This silsesquioxane derivative can also be used as an additive for enhancing flame retardancy, heat resistance, weatherability, an electrical insulating property, a surface characteristic, hardness, a dynamic strength and a chemical resistance of a polymer material. In the present invention, silsesquioxane is used as a general term of a compound obtained by hydrolyzing and condensing a trifunctional hydrolyzable silicon compound. In the following explanations, silsesquioxane shall be shown by a code PSQ.

BACKGROUND OF THE INVENTION

PSQ has so far been researched in many cases. For example, the general remark of PSQ written by Baney et al. is described in Chem. Rev. 1995, 95, 1409. According to this, confirmed to be present is PSQ having a structure such as an amorphous structure showing no fixed structure in addition to a ladder structure, a completely condensed structure and an incompletely condensed structure. The completely condensed structure comprises plural cyclic structures, and is a structure forming a closed space. And the form of the closed space is not restricted. The incompletely condensed structure shows a structure in which at least one portion in the completely condensed structure is not shut and in which a space is not closed.

Feher et al. obtained PSQ of an incompletely condensed structure by hydrolyzing cyclopentyl-trichlorosilane or cyclohexyltrichlorosilane in acetone (Organometallics, 1991, 10, 2556). Shchegolikhina et al. synthesized PSQ of a cyclic tetramer in which a terminal was turned into Si—O—Na by hydrolyzing phenyltributoxysilane in butanol using an equivalent mole of sodium hydroxide and an equivalent mole of water. Further, they synthesized PSQ of a cyclic tetramer in which a terminal was turned into Si—O—Na by reacting phenyltrichlorosilane-hydrolyzed product with an equivalent mole of sodium hydroxide in butanol (Organometallics, 2000, 19, 1077).

However, reported have been no examples in which PSQ having a completely condensed structure or an incompletely condensed structure is synthesized using the method of Shchegolikhina et al. Further, among PSQ having a completely condensed structure or an incompletely condensed structure, the kind of the compounds which are readily synthesized and isolated is restricted. Among them, the number of the commercially available compounds is further restricted. In recent years, PSQ derivatives obtained by introducing various functional groups into PSQ having a completely condensed structure or an incompletely condensed structure are commercially available from Hybrid Plastic Co., Ltd., and many uses are proposed.

However, the commercially available PSQ derivatives have only several kinds of fundamental skeletons including the skeletons having an organic silicon group of a bonding state other than $SiO_{3/2}$. Accordingly, that PSQ derivatives having a novel skeleton are provided is desirable in order to effectively make the best use of a PSQ derivative having a completely condensed structure or an incompletely condensed structure in wide uses. It is important as well that they can be produced at a lower cost for further shorter time as compared with in the past. Further, the existing PSQ derivatives have had the problems that they have an inferior compatibility with resins and therefore can not uniformly be mixed and that they are whitened when forming a coating film or bled out from a coating film, so that the addition amount is restricted. Accordingly, some of them could not sufficiently provide characteristics expected to PSQ. Hence, it is desirable for expanding the uses of PSQ, to provide a PSQ derivative which is improved in a compatibility with resins. The subject of the present invention is to solve the above problems on conventional silsesquioxanes by providing a novel PSQ derivative and a process for producing the same at a lower cost for shorter time.

DISCLOSURE OF THE INVENTION

The present inventors have found a novel PSQ derivative of an incompletely condensed type in which Na is bonded to PSQ of a cage type having eight Si atoms and a process for readily synthesizing the same by researching a hydrolytic method for a trifunctional hydrolyzable silicon compound. Also, they have obtained a PSQ derivative into which a functional group and the like can readily be introduced by using the above PSQ derivative as a starting raw material. Further, they have found that if a functional polymerizable group is introduced into the PSQ derivative, an oligomer or a polymer having the above PSQ derivative as a structural unit can be synthesized. That is, the present invention is composed of the following items [1] to [39].

[1] A Silsesquioxane Derivative Represented by Formula (1):

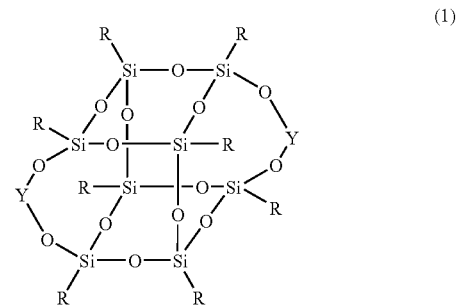

wherein each R in Formula (1) is a group independently selected from hydrogen, the group of alkyls having 1 to 45 carbon atoms, the group of substituted or non-substituted aryls and the group of substituted or non-substituted arylalkyls; Y is a group represented by Formula (a) or Formula (b); in the alkyl having 1 to 45 carbon atoms, optional hydrogen may be replaced by fluorine, and optional —$CH_2$— may be replaced by —O—, —CH=CH—, cycloalkylene or cycloalkenylene; in alkylene of the substituted or non-substituted arylalkyl, optional hydrogen may be replaced by fluorine, and optional —$CH_2$— may be replaced by —O—, —CH=CH— or cycloalkylene:

-continued

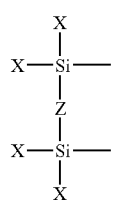
(b)

wherein X's in Formula (a) and Formula (b) each are independently hydrogen, halogen, a hydroxyl group or a monovalent organic group; and Z is —O—, —CH$_2$— or a single bond.

[2] The silsesquioxane derivative as described in the item [1], wherein at least one X in each of Formula (a) and Formula (b) is a group defined in the same manner as R.

[3] The silsesquioxane derivative as described in the item [1], wherein each R in Formula (1) is a group independently selected from the group of alkyls having 1 to 30 carbon atoms, and hydrogen; in the alkyl having 1 to 30 carbon atoms, optional hydrogen may be replaced by fluorine, and optional —CH$_2$— may be replaced by —O— or cycloalkylene; at least one X in each of Formula (a) and Formula (b) is a group selected from the group of alkyls having 1 to 45 carbon atoms, the group of substituted or non-substituted phenyls, and naphthyl; in the alkyl having 1 to 45 carbon atoms, optional hydrogen may be replaced by fluorine, and optional —CH$_2$— may be replaced by —O—, —CH=CH—, cycloalkylene or cycloalkenylene; in the substituted or non-substituted phenyl, optional hydrogen on the benzene ring may be replaced by halogen or alkyl having 1 to 18 carbon atoms; in the above alkyl having 1 to 18 carbon atoms, optional hydrogen may be replaced by fluorine, and optional —CH$_2$— may be replaced by —O—, —CH=CH— or phenylene; and, when the phenyl has plural substituents, the substituents may be the same group or different groups.

[4] The silsesquioxane derivative as described in the item [1], wherein each R in Formula (1) is a group independently selected from the group of alkenyls having 1 to 20 carbon atoms and the group of groups in which optional —CH$_2$— in alkyl having 1 to 20 carbon atoms is replaced by cycloalkenylene; in the alkenyl having 1 to 20 carbon atoms, optional hydrogen may be replaced by fluorine, and optional —CH$_2$— may be replaced by —O— or cycloalkylene; in the group in which optional —CH$_2$— in alkyl having 1 to 20 carbon atoms is replaced by cycloalkylene, optional hydrogen may be replaced by fluorine; and at least one X in each of Formula (a) and Formula (b) is a group defined in the same manner as X described in the item [3].

[5] The silsesquioxane derivative as described in the item [1], wherein each R in Formula (1) is a group independently selected from the group of substituted or non-substituted phenyls and naphthyl; in the substituted or non-substituted phenyl, optional hydrogen on the benzene ring may be replaced by halogen or alkyl having 1 to 10 carbon atoms; in the above alkyl having 1 to 10 carbon atoms, optional hydrogen may be replaced by fluorine, and optional —CH$_2$— may be replaced by —O—, —CH=CH—, cycloalkylene or phenylene; when the phenyl has plural substituents, the substituents may be the same group or different groups; and at least one X in each of Formula (a) and Formula (b) is a group defined in the same manner as X described in the item [3].

[6] The silsesquioxane derivative as described in the item [1], wherein each R in Formula (1) is a group independently selected from the group of substituted or non-substituted phenylalkyls; in phenyl of the substituted or non-substituted phenylalkyl, optional hydrogen on the benzene ring may be replaced by halogen or alkyl having 1 to 12 carbon atoms; in the above alkyl having 1 to 12 carbon atoms, optional hydrogen may be replaced by fluorine, and optional —CH$_2$— may be replaced by —O—, —CH=CH—, cycloalkylene or phenylene; in alkylene of the substituted or non-substituted phenylalkyl, the number of carbon atoms is 1 to 12, optional hydrogen may be replaced by fluorine, and optional —CH$_2$— may be replaced by —O— or cycloalkylene; when the phenyl has plural substituents, the substituents may be the same group or different groups; and at least one X in each of Formula (a) and Formula (b) is a group defined in the same manner as X described in the item [3].

[7] The silsesquioxane derivative as described in the item [1], wherein each R in Formula (1) is a group independently selected from the group of substituted or non-substituted phenylalkenyls; in phenyl of the substituted or non-substituted phenylalkenyl, optional hydrogen on the benzene ring may be replaced by halogen or alkyl having 1 to 12 carbon atoms; in the above alkyl having 1 to 12 carbon atoms, optional hydrogen may be replaced by fluorine, and optional —CH$_2$— may be replaced by —O—, —CH=CH—, cycloalkylene or phenylene; in alkenylene of the substituted or non-substituted phenylalkenyl the number of carbon atoms is 1 to 12, optional hydrogen may be replaced by fluorine, and optional —CH$_2$— may be replaced by —O— or cycloalkylene; when the phenyl has plural substituents, the substituents may be the same group or different groups; and at least one X in each of Formula (a) and Formula (b) is a group defined in the same manner as X described in the item [3].

[8] The silsesquioxane derivative as described in the item [1], wherein each R in Formula (1) is a group independently selected from the group of alkyls having 1 to 8 carbon atoms, the group of substituted or non-substituted phenyls, the group of substituted or non-substituted phenylalkyls, and naphthyl; in the alkyl having 1 to 8 carbon atoms, optional hydrogen may be replaced by fluorine, and optional —CH$_2$— may be replaced by —O—, —CH=CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; when the phenyl has plural substituents, the substituents may be the same group or different groups; and at least one X in each of Formula (a) and Formula (b) is a group defined in the same manner as X described in the item [3].

[9] The silsesquioxane derivative as described in the item [1], wherein all of R's in Formula (1) are the same group selected from the group of alkyls having 1 to 8 carbon atoms, the group of substituted or non-substituted phenyls, the group of substituted or non-substituted phenylalkyls, and naphthyl; in the alkyl having 1 to 8 carbon atoms, optional hydrogen may be replaced by fluorine, and optional —CH$_2$— may be replaced by —O—, —CH=CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH═CH— or cycloalkylene; when the phenyl has plural substituents, the substituents may be the same group or different groups; and at least one X in each of Formula (a) and Formula (b) is a group defined in the same manner as X as described in the item [3].

[10] The silsesquioxane derivative as described in the item [1], wherein all of R's in Formula (1) are the same group selected from the group of substituted or non-substituted phenyls, the group of substituted or non-substituted phenylalkyls, and naphthyl; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH═CH— or cycloalkylene; when the phenyl has plural substituents, the substituents may be the same group or different groups; and at least one X in each of Formula (a) and Formula (b) is a group defined in the same manner as X as described in the item [3].

[11] The silsesquioxane derivative as described in the item [1], wherein all of R's in Formula (1) are non-substituted phenyls, and at least one X in each of Formula (a) and Formula (b) is a group defined in the same manner as X described in the item [3].

[12] The silsesquioxane derivative as described in the item [1], wherein each R in Formula (1) is a group independently selected from the group of alkyls having 1 to 45 carbon atoms, the group of substituted or non-substituted aryls and the group of substituted or non-substituted arylalkyls; in the alkyl having 1 to 45 carbon atoms, optional hydrogen may be replaced by fluorine, and optional —CH$_2$— may be replaced by —O—, —CH═CH—, cycloalkylene or cycloalkenylene; in alkylene of the substituted or non-substituted arylalkyl, optional hydrogen may be replaced by fluorine, and optional —CH$_2$— may be replaced by —O—, —CH═CH— or cycloalkylene; and at least one X in each of Formula (a) and Formula (b) is a functional group or a group having a functional group.

[13] The silsesquioxane derivative as described in the item [12], wherein each R in Formula (1) as described in the item [1] is a group independently selected from hydrogen and the group of alkyls having 1 to 30 carbon atoms; in the alkyl having 1 to 30 carbon atoms, optional hydrogen may be replaced by fluorine, and optional —CH$_2$— may be replaced by —O— or cycloalkylene; and the functional group is a group selected from —H (bonded to Si), —F, —Cl, —Br, —OH, —CF$_3$, perfluoroalkyl, alkoxy, —COOH, 2-oxapropane-1,3-dioyl, polyalkyleneoxy, ester, epoxy, an oxetane ring, —NH$_2$, —CN, —NCO, alkenyl, cycloalkenyl, —SH and —PH$_2$.

[14] The silsesquioxane derivative as described in the item [12], wherein each R in Formula (1) as described in the item [1] is a group independently selected from the group of alkenyls having 1 to 20 carbon atoms and the group of groups in which optional —CH$_2$— in alkyl having 1 to 20 carbon atoms is replaced by cycloalkenylene; in the alkenyl having 1 to 20 carbon atoms, optional hydrogen may be replaced by fluorine, and optional —CH$_2$— may be replaced by —O— or cycloalkylene; in the group in which optional —CH$_2$— in alkyl having 1 to 20 carbon atoms is replaced by cycloalkenylene, optional hydrogen may be replaced by fluorine; and the functional group is a group defined in the same manner as the functional group as described in the item [13].

[15] The silsesquioxane derivative as described in the item [12], wherein each R in Formula (1) as described in the item [1] is a group independently selected from the group of substituted or non-substituted phenyls and naphthyl; in the substituted or non-substituted phenyl, optional hydrogen on the benzene ring may be replaced by halogen or alkyl having 1 to 10 carbon atoms; in the above alkyl having 1 to 10 carbon atoms, optional hydrogen may be replaced by fluorine, and optional —CH$_2$— may be replaced by —O—, —CH═CH—, cycloalkylene or phenylene; when the phenyl has plural substituents, the substituents may be the same group or different groups; and the functional group is a group defined in the same manner as the functional group as described in the item [13].

[16] The silsesquioxane derivative as described in the item [12], wherein each R in Formula (1) as described in the item [1] is a group independently selected from the group of substituted or non-substituted phenylalkyls; in phenyl of the substituted or non-substituted phenylalkyl, optional hydrogen on the benzene ring may be replaced by halogen or alkyl having 1 to 12 carbon atoms; in the above alkyl having 1 to 12 carbon atoms, optional hydrogen may be replaced by fluorine, and optional —CH$_2$— may be replaced by —O—, —CH═CH—, cycloalkylene or phenylene; in alkylene of the substituted or non-substituted phenylalkylthe number of carbon atoms is 1 to 12, optional hydrogen may be replaced by fluorine, and optional —CH$_2$— may be replaced by —O— or cycloalkylene; when the phenyl has plural substituents, the substituents may be the same group or different groups; and the functional group is a group defined in the same manner as the functional group as described in the item [13].

[17] The silsesquioxane derivative as described in the item [12], wherein each R in Formula (1) described in the item [1] is a group independently selected from the group of substituted or non-substituted phenylalkenyls; in phenyl of the substituted or non-substituted phenylalkenyl, optional hydrogen on the benzene ring may be replaced by halogen or alkyl having 1 to 12 carbon atoms; in the above alkyl having 1 to 12 carbon atoms, optional hydrogen may be replaced by fluorine, and optional —CH$_2$— may be replaced by —O—, —CH═CH—, cycloalkylene or phenylene; in alkenylene of the substituted or non-substituted phenylalkenyl, the number of carbon atoms is 1 to 12, optional hydrogen may be replaced by fluorine, and optional —CH$_2$— may be replaced by —O— or cycloalkylene; when the phenyl has plural substituents, the substituents may be the same group or different groups; and the functional group is a group defined in the same manner as the functional group as described in the item [13].

[18] The silsesquioxane derivative as described in the item [12], wherein each R in Formula (1) as described in the item [1] is a group independently selected from the group of alkyls having 1 to 8 carbon atoms, the group of substituted or non-substituted phenyls, the group of substituted or non-substituted phenylalkyls, and naphthyl; in the alkyl having 1 to 8 carbon atoms, optional hydrogen may be replaced by fluorine, and optional —CH$_2$— may be replaced by —O—, —CH═CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —$CH_2$— may be replaced by —O—, —CH═CH— or cycloalkylene; when the phenyl has plural substituents, the substituents may be the same group or different groups; and the functional group is a group defined in the same manner as the functional group as described in the item [13].

[19] The silsesquioxane derivative as described in the item [12], wherein all of R's in Formula (1) as described in the item [1] are the same group selected from the group of alkyls having 1 to 8 carbon atoms, the group of substituted or non-substituted phenyls, the group of substituted or non-substituted phenylalkyls, and naphthyl; in the alkyl having 1 to 8 carbon atoms, optional hydrogen may be replaced by fluorine, and optional —$CH_2$— may be replaced by —O—, —CH═CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —$CH_2$— may be replaced by —O—, —CH═CH— or cycloalkylene; when the phenyl has plural substituents, the substituents may be the same group or different groups; and the functional group is a group defined in the same manner as the functional group as described in the item [13].

[20] The silsesquioxane derivative as described in the item [12], wherein all of R's in Formula (1) described in the item [1] are the same group selected from the group of substituted or non-substituted phenyls, the group of substituted or non-substituted phenylalkyls, and naphthyl; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —$CH_2$— may be replaced by —O—, —CH═CH— or cycloalkylene; when the phenyl has plural substituents, the substituents may be the same group or different groups; and the functional group is a group defined in the same manner as the functional group as described in the item [13].

[21] The silsesquioxane derivative as described in the item [12], wherein all of R's in Formula (1) as described in the item [1] are non-substituted phenyls, and the functional group is a group defined in the same manner as the functional group as described in the item [13].

[22] The silsesquioxane derivative as described in any item of [1] to [21], wherein at least one X in each of Formula (a) and Formula (b) as described in the item [1] is a polymerizable group.

[23] The silsesquioxane derivative as described in the item [22], wherein the polymerizable group is a polymerizable double bond, epoxy or a group having an oxetane ring.

[24] The silsesquioxane derivative as described in any item of [12] to [21], wherein at least one X in each of Formula (a) and Formula (b) as described in the item [1] is a group having 2-oxapropane-1,3-dioyl.

[25] The silsesquioxane derivative as described in any item of [1] to [21], wherein at least one X in each of Formula (a) and Formula (b) as described in the item [1] is alkyl halide.

[26] A polymer obtained using the silsesquioxane derivative as described in the item [22].

[27] A polymer obtained using the silsesquioxane derivative as described in the item [23].

[28] A polymer obtained using the silsesquioxane derivative as described in the item [24].

[29] A production process for the silsesquioxane derivative as described in the item [1], characterized by reacting a silsesquioxane derivative represented by Formula (2) with a silicon compound having at least two chlorines:

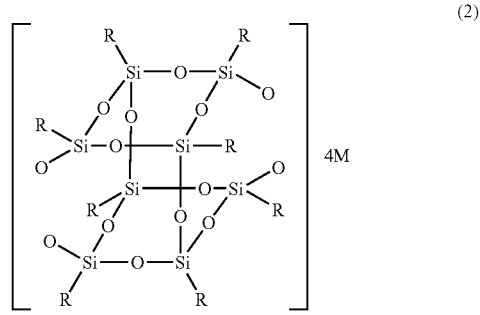

wherein in Formula (2), R is the same as R in Formula (1) as described in the item [1], and M is a monovalent alkaline metal atom.

[30] The production process as described in the item [29], wherein the silicon compound having at least two chlorines is a compound represented by Formula (3):

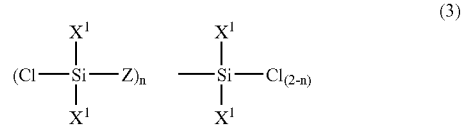

wherein in Formula (3), n is 0 or 1; Z is —O—, —$CH_2$— or a single bond; each $X^1$ is a group independently selected from hydrogen, halogen, the group of alkyls having 1 to 45 carbon atoms, the group of substituted or non-substituted aryls and the group of substituted or non-substituted arylalkyls; in the alkyl having 1 to 45 carbon atoms, optional hydrogen may be replaced by fluorine, and optional —$CH_2$— may be replaced by —O—, —CH═CH—, cycloalkylene or cycloalkenylene; in alkylene of the substituted or non-substituted arylalkyl, optional hydrogen may be replaced by fluorine, and optional —$CH_2$— may be replaced by —O—, —CH═CH— or cycloalkylene.

[31] The production process as described in the item [29], wherein the silicon compound having at least two chlorines is a compound represented by Formula (4):

wherein X¹ in Formula (4) is defined in the same manner as X¹ in Formula (3) as described in the item [30].

[32] The production process as described in the item [29], wherein the silicon compound having at least two chlorines is a compound represented by Formula (5):

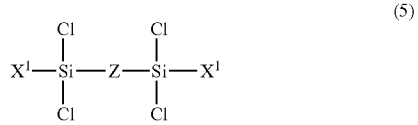

wherein Z and X¹ in Formula (5) are defined in the same manner as Z and X¹ in Formula (3) as described in the item [30].

[33] A silsesquioxane derivative represented by Formula (2):

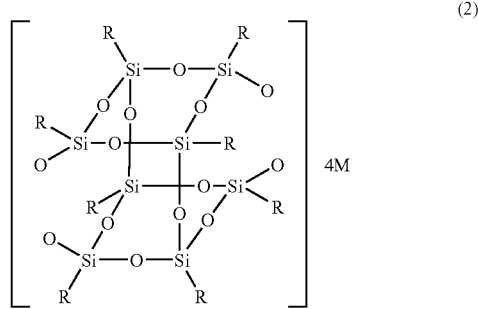

wherein in Formula (2), R is the same as R in Formula (1) as described in the item [1], and M is a monovalent alkaline metal atom.

[34] The silsesquioxane derivative as described in the item [33], wherein R is defined in the same manner as R as described in any of the items [2] to [11].

[35] A production process for the silsesquioxane derivative as described in the item [33], characterized by using a silicon compound represented by Formula (6):

wherein in Formula (6), R is the same as R in Formula (2) as described in the item [33], and A is a hydrolyzable group.

[36] The production process as described in the item [35], wherein a monovalent alkaline metal hydroxide and water are used to hydrolyze and condense the silicon compound represented by Formula (6).

[37] The production process as described in the item [36], wherein the monovalent alkaline metal hydroxide is sodium hydroxide or potassium hydroxide, and alcohols in addition to the alkaline metal hydroxide and water are allowed to be present.

[38] The production process as described in any of the items [35] to [37], wherein A in Formula (6) as described in the item [35] is chlorine or alkyloxy having 1 to 4 carbon atoms.

[39] The production process as described in the item [35], wherein R in Formula (6) is defined in the same manner as R described in any of the items [2] to [11].

The terms used in the present invention are defined as follows. Each of alkyl and alkylene may be a linear group or a branched group. This shall apply as well to a case in which optional hydrogen is replaced by halogen or a cyclic group and a case in which optional —CH$_2$— is replaced by —O—, —CH=CH—, cycloalkylene, cycloalkenylene or phenylene. The term "optional" used in the present invention shows that not only a position but also a number is optional. When the number is plural, they may be replaced by different groups respectively. For example, when two —CH$_2$— in alkyl are replaced by —O— and —CH=CH—, it shows alkoxyalkenyl or alkenyloxyalkyl. In this case, all groups of alkoxy, alkenylene, alkenyl and alkylene may be linear groups or branched groups. However, when it is described that optional —CH$_2$— is replaced by —O—, plural continuous —CH$_2$— are not replaced by —O—. Halogen is fluorine, chlorine and bromine unless other wise described, and preferred halogen is fluorine and chlorine.

In the following explanations, the PSQ derivative represented by Formula (1) shall be shown by PSQ (1). The PSQ derivative represented by Formula (2) shall be shown by PSQ (2). The compound represented by Formula (3), the compound represented by Formula (4), the compound represented by Formula (5) and the compound represented by Formula (6) shall be shown by the compound (3), the compound (4), the compound (5) and the compound (6), respectively. Further, tetrachlorosilane, the compound (3), the compound (4) and the compound (5) shall be shown by a general term of the chlorinated silicon compound.

The PSQ derivative of the present invention is represented by Formula (1):

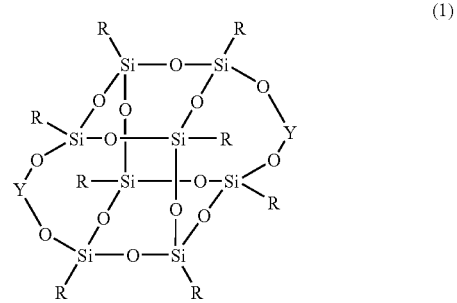

In Formula (1), R is a group independently selected from hydrogen, the group of alkyls having 1 to 45 carbon atoms, the group of substituted or non-substituted aryls and the group of substituted or non-substituted arylalkyls. All of R's are preferably the same group, but eight R's may be constituted by different groups. The examples of a case in which eight R's are constituted by different groups are a case in which they are constituted by two or more alkyls, a case in which they are constituted by two or more aryls, a case in which they are constituted by two or more aralkyls, a case in which they are constituted by hydrogen and at least one aryl, a case in which they are constituted by at least one alkyl and at least one aryl, a case in which they are constituted by at least one alkyl and at least one aralkyl, and a case in which they are constituted by at least one aryl and at least one aralkyl. They may be combinations other than the above examples. The compound (1) having at least two different R's can be obtained by using two or more compounds (6) when producing the compound (2). The compound (2) shall be described later.

When R is alkyl, the number of carbon atoms is 1 to 45. The preferred carbon number is 1 to 30. More preferred carbon number is 1 to 8. Optional hydrogen thereof may be replaced by fluorine, and optional —$CH_2$— thereof may be replaced by —O—, —CH=CH—, cycloalkylene or cycloalkenylene. The preferred examples of the alkyl are non-substituted alkyl having 1 to 30 carbon atoms, alkoxyalkyl having 2 to 29 carbon atoms, a group in which one —$CH_2$— in alkyl having 1 to 8 carbon atoms is replaced by cycloalkylene, alkenyl having 2 to 20 carbon atoms, alkenyloxyalkyl having 2 to 20 carbon atoms, alkyloxyalkenyl having 2 to 20 carbon atoms, a group in which one —$CH_2$— in alkyl having 1 to 8 carbon atoms is replaced by cycloalkenylene, and groups in which optional hydrogens in the respective groups given above are replaced by fluorine. Cycloalkylene and cycloalkenylene have a preferred carbon number of 3 to 8.

The examples of the non-substituted alkyl having 1 to 30 carbon atoms are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethylpentyl, nonyl, decyl, undecyl, dodecyl, tetradecyl, hexadecyl, octadecyl, eicosyl, docosyl and triacontyl. The examples of the fluorinated alkyl having 1 to 30 carbon atoms are 3,3,3-trifluoropropyl, 3,3,4,4,5,5,6,6,6-nonadecafluoro-hexyl, tridecafluoro-1,1,2,2-tetrahydrooctyl, heptadecafluoro-1,1,2,2-tetrahydrodecyl, perfluoro-1H,1H,2H,2H-dodecyl and perfluoro-1H,1H,2H,2H-tetradecyl. The examples of the alkoxyalkyl having a carbon number of 2 to 29 are 3-methoxypropyl, methoxyethoxyundecyl and 3-heptafluoroisopropoxypropyl. The examples of the group in which one —$CH_2$— in alkyl having 1 to 8 carbon atoms is replaced by cycloalkylene are cyclohexylmethyl, adamantaneethyl, cyclopentyl, cyclohexyl, 2-bicycloheptyl and cyclooctyl. Cyclohexyl is an example in which —$CH_2$— in methyl is replaced by cyclohexylene. Cyclohexylmethyl is an example in which —$CH_2$— in ethyl is replaced by cyclohexylene.

The examples of the alkenyl having 2 to 20 carbon atoms are ethenyl, 2-propenyl, 3-butenyl, 5-hexenyl, 7-octenyl, 10-undecenyl and 21-docosenyl. The examples of the alkenyloxyalkyl having 2 to 20 carbon atoms are allyloxyundecyl. The examples of the group in which one —$CH_2$— in alkyl having 1 to 8 carbon atoms is replaced by cycloalkenylene are 2-(3-cyclohexenyl)ethyl, 5-(bicycloheptenyl)ethyl, 2-cyclopentenyl, 3-cyclohexenyl, 5-norbornene-2-yl and 4-cyclooctenyl.

The examples of a case, in which R in Formula (1) is substituted or non-substituted aryl, are phenyl in which optional hydrogen may be replaced by halogen or alkyl having 1 to 10 carbon atoms, and non-substituted naphthyl. The preferred examples of halogen are fluorine, chlorine and bromine. In the alkyl having 1 to 10 carbon atoms, optional hydrogen may be replaced by fluorine, and optional —$CH_2$— may be replaced by —O—, —CH=CH— or phenylene. That is, the preferred examples of the case, in which R is substituted or non-substituted aryl, are non-substituted phenyl, non-substituted naphthyl, alkylphenyl, alkyloxyphenyl, alkenylphenyl, phenyl having a substituent of a group, in which optional —$CH_2$— in alkyl having 1 to 10 carbon atoms is replaced by phenylene, and groups in which optional hydrogens in the respective groups given above are replaced by halogen.

The examples of halogenated phenyl are pentafluorophenyl, 4-chrorophenyl and 4-bromophenyl. The examples of alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tis (1-methylethyl)phenyl. The examples of alkyloxyphenyl are 4-methoxyphenyl, 4-ethoxy-phenyl, 4-propoxyphenyl, 4-butoxyphenyl, 4-pentyloxyphenyl, 4-heptyloxyphenyl, 4-decyloxyphenyl, 4-octadecyloxyphenyl, 4-(1-methylethoxy)phenyl, 4-(2-methylpropoxy)phenyl and 4-(1,1-dimethylethoxy)phenyl. The examples of alkenylphenyl are 4-ethenylphenyl, 4-(1-methylethenyl)phenyl and 4-(3-butenyl)phenyl.

The examples of phenyl having a substituent of a group, in which optional —$CH_2$— in alkyl having 1 to 10 carbon atoms is replaced by phenylene, are 4-(2-phenylethenyl)phenyl, 4-phenyloxyphenyl, 3-phenylmethyl-phenyl, biphenyl and terphenyl. 4-(2-Phenylethenyl)phenyl is an example in which one —$CH_2$— in ethyl of ethylphenyl is replaced by phenylene and in which one more —$CH_2$— is replaced by —CH=CH—.

The examples of phenyl, in which a part of hydrogens on the benzene ring is replaced by halogen and the other hydrogens are replaced by alkyl, alkyloxy or alkenyl, are 3-chloro-4-methylphenyl, 2,5-dicholoro-4-methylphenyl, 3,5-dichloro-4-methylphenyl, 2,3,5-trichloro-4-methylphenyl, 2-3-6-trichloro-4-methylphenyl, 3-bromo-4-methylphenyl, 2,5-dibromo-4-methylphenyl, 3,5-dibromo-4-methylphenyl, 2-3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-ethenyl-2,3,5,6-tetrafluorophenyl.

Next, a case in which R in Formula (1) is substituted or non-substituted arylalkyl shall be given. In alkylene in the arylalkyl, optional hydrogen may be replaced by fluorine, and optional —$CH_2$— may be replaced by —O—, —CH=CH— or cycloalkylene. The preferred examples of the arylalkyl are phenylalkyls. In this case, the preferred carbon number of the alkylene is 1 to 12, and more preferred carbon number is 1 to 8. The examples of non-substituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

In the phenylalkyl, optional hydrogen on the benzene ring may be replaced by halogen or alkyl having 1 to 12 carbon atoms. In the above alkyl having 1 to 12 carbon atoms, optional hydrogen may be replaced by fluorine, and optional —$CH_2$— may be replaced by —O—, —CH=CH—, cycloalkylene or phenylene. The examples of the phenylalkyl, in which optional hydrogen of phenyl is replaced by fluorine, are 4-fluorophenylmethyl, 2,3,4,5,6-pentafluorophenylmethyl, 2-(2,3,4,5,6-pentafluorophenyl)-ethyl, 3-(2,3,4,5,6-pentafluorophenyl)propyl, 2-(2-fluorophenyl)propyl and 2-(4-fluorophenyl)propyl.

The examples of the phenylalkyl, in which optional hydrogen on the benzene ring is replaced by chlorine, are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenylmethyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4- chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chloropheyl)ethyl, 1-(4-chlorophenyl)ethyl, 2-(4-chlorophenyl)propyl, 2, (2-chlorophenyl)propyl and 1-(4-chlorophenyl)butyl.

The examples of the phenylalkyl, in which optional hydrogen on the benzene ring is replaced by bromine, are 2-bromophenylmethyl, 4-bromophenylmethyl, 2,4-dibromophenyl-methyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl and 2-(4-bromophenyl)propyl.

The examples of the phenylalkyl, in which optional hydrogen on the benzene ring is replaced by alkyl having 1 to 12 carbon atoms, are 2-methylphenylmethyl, 3-methylphenylmethyl, 4-methylphenylmethyl, 4-dodecylphenylmethyl, 2,5-dimethylphenylmethyl, 2-(4-methylphenyl)ethyl, 2-(3-methylphenyl) ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethlphenyl)propyl, 2-(2,4-dimethylphenyl)propyl, 2-(3,4-dimethylphenyl)propyl, 2-(2,5-dimethylphenyl)butyl, 4-(1-methylethyl)phenylmethyl, 2-(4-(1,1-dimethylethyl)phenyl)ethyl, 2-(4-(1-methylethyl)phenyl)propyl and 2-(3-(1-methylethyl)phenyl)-propyl.

The examples of the phenylalkyl, in which optional hydrogen on the benzene ring is replaced by alkyl having 1 to 12 carbon atoms and hydrogens in the alkyl are replaced by fluorinesi, are 3-trifluoromethylphenylmethyl, 2-(4-trifluoromethylphenyl)ethyl, 2-(4-nonafluorobutylphenyl)-ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)-ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexylphenyl)ethyl, 2-(4-heptadecafluorooctylphenyl)propyl and 1-methyl-1-(4-heptadecafluorooctylphenyl)ethyl.

The examples of the phenylalkyl, in which optional hydrogen on the benzene ring is replaced by alkyl having 1 to 12 carbon atoms and —CH$_2$— in the alkyl is replaced by —CH=CH—, are 2-(4-ethenylphenyl)ethyl, 1-(4-ethenylphenyl)ethyl and 1-(2-(2-propenyl)phenyl)ethyl. The examples of the phenylalkyl, in which optional hydrogen on the benzene ring is replaced by alkyl having 1 to 12 carbon atoms and —CH$_2$— in the alkyl is replaced by —O—, are 4-methoxyphenylmethyl, 3-methoxyphenylmethyl, 4-ethoxyphenyl-methyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, (3-methoxymethylphenyl)ethyl and 3-(2-nonadecafluorodecenyloxylphenyl)propyl.

The examples of the phenylalkyl in which optional hydrogen on the benzene ring is replaced by alkyl having 1 to 12 carbon atoms and one of —CH$_2$— in the alkyl is replaced by cycloalkylene are, to give the examples including an example in which one more —CH$_2$— is replaced by —O—, cyclopentylphenylmethyl, cyclopentyloxyphenylmethyl, cyclohexylphenylmethyl, cyclohexylphenylethyl, cyclohexylphenylpropyl and cyclohexyloxyphenylmethyl. The examples of the phenylalkyl in which optional hydrogen on the benzene ring is replaced by alkyl having 1 to 12 carbon atoms and in which one of —CH$_2$— in the alkyl is replaced by phenylene are, to give the examples including an example in which one more —CH$_2$— is replaced by —O—, 2-(4-phenoxyphenyl)ethyl, 2-(4-phenoxyphenyl)propyl, 2-(2-phenoxyphenyl)propyl, 4-biphenylmethyl, 3-biphenylethyl, 4-biphenylethyl, 4-biphenylpropyl, 2-(2-biphenyl)propyl and 2-(4-biphenyl)propyl.

The examples of the phenylalkyl, in which at least two optional hydrogens on the benzene ring are replaced by different groups, are 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenyl-methyl, 2,3,4,6-tetrachloro-5-methylphenylmethyl, 2,3,4,5-tetrachloro-6-methylphenylmethyl, 4-chloro-3,5-dimethylphenylmethyl, 2-chloro-3,5-dimethylphenylmethyl, 2,4-dichloro-3,5-dimethylphenylmethyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenylmethyl, 2,3,5-tribromo-4-methylphenylmethyl, 2,3,5,6-tetrabromo-4-methylphenylmethyl and 11-(3-chloro-4-methoxyphenyl)undecyl.

The most preferred examples of phenyl in the phenylalkyl are non-substituted phenyl and phenyl having at least one of fluorine, alkyl having 1 to 4 carbon atoms, ethenyl and methoxy as a substituent.

The examples of the phenylalkyl, in which —CH$_2$— in alkylene is replaced by —O—, —CH=CH— or cycloalkylene, are 3-phenoxypropyl, 1-phenylethenyl, 2-phenylethenyl, 3-phenyl-2-propenyl, 4-phenyl-4-pentenyl, 13-phenyl-12-tridecenyl, phenylcyclohexyl and phenoxycyclohexyl. The examples of the phenylalkenyl, in which optional hydrogen on the benzene ring is replaced by fluorine or methyl, are 4-fluorophenylethenyl, 2,3-difluorophenylethenyl, 2,3,4,5,6-pentafluorophenylethenyl and 4-methylphenylethenyl.

Among these groups, the preferred example of R is a group selected from the group of the alkyls having 1 to 8 carbon atoms, the group of the substituted or non-substituted phenyls, the group of the substituted or non-substituted phenylalkyls, and naphthyl. More preferred example of R is a group selected from the group of the substituted or non-substituted phenyls, the group of the substituted or non-substituted phenylalkyls, and naphthyl. In the above alkyl having 1 to 8 carbon atoms, optional hydrogen may be replaced by fluorine, and optional —CH$_2$— may be replaced by —O—, —CH=CH—, cycloalkylene or cycloalkenylene. In the substituted or non-substituted phenyl, optional hydrogen may be replaced by halogen, methyl or methoxy. In the substituted or non-substituted phenylalkyl, the number of carbon atoms of alkylene thereof is 1 to 8, optional hydrogen on the benzene ring may be replaced by fluorine, alkyl having 1 to 4 carbon atoms, ethenyl or methoxy, and optional —CH$_2$— may be replaced by —O—, —CH=CH— or cycloalkylene. In the above groups, when the phenyl has plural substituents, the substituents may be the same group or different groups. All of R's in Formula (1) are preferably the same group selected from these preferred examples of R.

The specific examples of more preferred R are non-substituted phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-ethenylphenylethyl, 1-(4-ethenylphenyl)ethyl, 4-methoxyphenylpropyl and phenoxypropyl. Among the above examples, non-substituted phenyl is most preferred.

Y in Formula (1) is a group represented by Formula (a) or Formula (b):

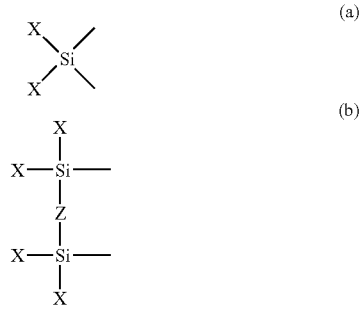

wherein X's in Formula (a) and Formula (b) each are independently hydrogen, halogen, a hydroxyl group or a monovalent organic group. In each of Formula (a) and Formula (b), at least one X is preferably the monovalent organic group. The preferred organic group is a functional group or a group having a functional group. Z in Formula (b) is —O—, —CH$_2$— or a single bond. Preferred Z is —O—. The group represented by Formula (a) or Formula (b) is introduced by reacting the PSQ (2) described above with a chlorinated silicon compound.

The PSQ (1) of the present invention can be produced by reacting the PSQ (2) with a chlorinated silicon compound in an organic solvent in the presence or the absence of a base. The PSQ (2) can be produced by hydrolyzing and condensing the silicon compound shown by the compound (6) in the presence of a monovalent alkaline metal hydroxide and water.

A use amount of the chlorinated silicon compound is 2 to 400 in terms of a mole ratio to the PSQ (2). The preferred mole ratio 2 to 100. More preferred mole ratio 2 to 50. A theoretical use amount of the chlorinated silicon compound is 2 in terms of a mole ratio to the PSQ (2), and therefore the unreacted chlorinated silicon compound has to be removed after finishing the reaction. The chlorinated silicon compound having a low boiling point can be removed by distillation. When can not be removed by distillation, the chlorinated silicon compound is removed by hydrolysis. In order to readily separate the resulting hydrolysate from the PSQ (1), a use amount of the chlorinated silicon compound is preferably 400 or less in terms of a mole ratio to the PSQ (2). It is very difficult to separate the PSQ (2) from the PSQ (1). Accordingly, in order to prevent the unreacted PSQ (2) from remaining, a use amount of the chlorinated silicon compound is preferably 2 or more in terms of a mole ratio to the PSQ (2).

The preferred organic solvent used in the above reaction is a solvent which is less liable to dissolve the PSQ (2) or which does not dissolve it at all. The examples thereof are hydrocarbon type solvents such as hexane, heptane, benzene and toluene, ether type solvents such as diethyl ether and tetrahydrofuran, ester type solvents such as ethyl acetate and halogenated hydrocarbon type solvents such as chloroform. The above solvents may be used in a mixture. A preferred use amount of the organic solvent is 1 to 400 times based on the weight of the PSQ (2). More preferred use amount is 1 to 100 times. The reaction is accompanied with heat generation, and therefore the organic solvent is preferably used in the same amount or more based on the weight of the PSQ (2) in order to readily control the reaction. In order to prevent the reaction time from being extended, a use amount of the organic solvent is preferably 100 times or less based on the weight of the PSQ (2).

The reaction of the PSQ (2) with the chlorinated silicon compound is accelerated by the presence of a base. Accordingly, the above reaction is preferably carried out in the presence of a base. The preferred base is amine. The example of the preferred amine is tertiary amine such as triethylamine. A preferred use amount of the base is 0.01 to 400 in terms of a mole ratio based on the PSQ (2). The preferred mole ratio is 0.1 to 100. More preferred mole ratio 0.2 to 10. The base of 0.1 or more in terms of a mole ratio based on the PSQ (2) is preferably used in order to obtain the PSQ (1) at a good yield. The base has an action to subject the hydrolysate of the chlorinated silicon compound to polycondensation. Accordingly, when a use amount of the organic solvent is small, it has to be avoided to use the base in a large amount, but when a use amount of the organic solvent is large, the base may be used in an amount of up to about 400 in terms of a mole ratio based on the PSQ (2). If a use amount of the base falls in the above range, the possibility to hinder a hydrolysate formed at a step after finishing the reaction from being separated is small. However, considering the volume efficiency, a preferred use amount of the base is 0.01 to 100 in terms of a mole ratio based on the PSQ (2).

The reaction time is varied depending on the kind of the chlorinated silicon compound used and the solvent, and it is usually several minutes to several hours. The reaction temperature shall not specifically be restricted and may be usually a room temperature. Thus, silsesquioxane having a functional group can be synthesized.

The preferred examples of the chlorinated silicon compound are tetrachlorosilane and the compound (3) to the compound (5). The examples of the compound (3) are acetoxyethylmethyldichlorosilane, acetoxypropylmethyldichlorosilane, (3-acryloyloxypropyl)-methyldichlorosilane, allyl(chloropropyl)dichlorosilane, allyl(2-cyclohexenylethyl)dichlorosilane, allyldichlorosilane, allylhexyldichlorosilane, allylmethyldichlorosilane, allylphenyldichlorosilane, 5-(bicycloheptenyl)methyldichlorosilane, butenylmethyldichlorosilaneiii, t-butyl-methyldichlorosilane, n-butylmethyldichlorosilane, t-butyldichlorosilane, t-butylphenyldichloro-silane, 2-(methoxycarbonyl)ethylmethyldichlorosilane, 2-chloroethyl-methyldichlorosilane, chloromethylmethyldichlorosilane, ((chloromethyl)phenethyl)methyldichlorosilane, 2-(chloromethyl)-propylmethyldichlorosilane, chlorophenyl-methyldichlorosilane, 3-chloropropylmethyldichlorosilane, 3-chloropropylphenyldichlorosilane, (3-cyanobutyl) methyl-dichlorosilane, 2-cyanoethylmethyldichlorosilane, 3-cyanopropylmethyldichlorosilane, 3-cyanopropylphenyldichlorosilane, (3-cyclohexenylethyl)-methyldichlorosilane, cyclohexenylmethyldichlorosilane, cyclobutenyl-dichlorosilane, cyclopropenyldichlorosilane, n-decylmethyldichlorosilane, diallyldichlorosilane, n-butyl-dichlorosilane, di-t-butyldichlorosilane, 1,1-dichloro-3,3-dimethyl-1,3-disilabutane, 1,3-dichloro-1,3-diphenyl-1,3-dimethyldisiloxane, (dichloromethyl)-methyldichlorosilane, 1,3-dichlorotetramethyldisiloxane, 1,3-dichloro-tetraphenyldisiloxane, dichlorotetramethyldisilane, dicyclohexyldichlorosilane, dicyclopentyl-dichlorosilane, diethyldichlorosilane, di-n-hexydichlorosilane, diisopropyldichlorosilane, dimesityldichlorosilanek, dimethyldichlorosilane, di-n-octyldichlorosilane, diphenyldichlorosilane, di(p-tolyl)dichlorosilane, divinyldichlorosilane, 1,3-divinyl-1,3-dimethyl-1,3-dichlorosilane, ethyldichlorosilane, ethylmethyldichlorosilane, (heptadecafluoro-1,1,2,2-tetrahydrodecyl)-methyldichlorosilane, n-heptyl-methyldichlorosilane, hexyldichlorosilane, hexylmethyldichlorosilane, isobutylmethyldichlorosilane, isopropylmethyl-dichlorosilane, methacryloyloxypropyl-methyldichlorosilane, 3-(p-metoxyphenyl)propyl-methyldichlorosilane, methylpentyldichlorosilane, p-(methylphenethyl)-methyldichlorosilane, 2-methyl-2-phenylethyldichlorosilane, 3,3,4,4,5,5,6,6,6-nonafluorohexylmethyldichlorosilane, n-octyl-methyldichlorosilane, phenethylmethyl-dichlorosilane, phenyldichlorosilane, phenylethyl-dichlorosilane, phenylmethyldichlorosilane, (3-phenylpropyl)methyl-dichlorosilane, 1-allylmethyl-dichlorosilane, propylmethyldichlorosilane, p-tolylmethyldichlorosilane, (tridecafluoro-1,1,2,2-tetrahydrooctyl)methyl-dicholorosilane, (3,3,3-trifluoropropyl)methyl-dichlorosilane, vinylethyl-dichlorosilane, vinylmethyldichlorosilane, vinyloctyldichlorosilane, vinylphenyldichlorosilane, methyldichlorosilane, 1,3-dichloro-1,3-dimethyl-disiloxane, 1,3-dichloro-1,3-dimethyl-1,3-divinyldisiloxane and 1,3-dichloro-1,3-diphenyl-disiloxane.

The examples of the compound (4) are acetoxyethyltrichlorosilane, (3-acryloyloxypropyl)-trichlorosilane, admantylethyltrichlorosilane, allyltrichlorosilane, benzyltrichlorosilane, 5-(bicycloheptenyl)trichlorosilane, 2-(bicycloheptyl)-trichlorosilane, 2-bromoethyltrichlorosilane, bromophenyl-trichlorosilane, 3-bromopropyl-trichlorosilane, p-(t-butyl)phenethyltrichlorosilane, n-butyltrichlorosilane, t-butyltrichlorosilane, 2-(methoxycarbonyl)ethyl-trichlorosilane, 1-chloroethyltrichlorosilane, 2-chloroethyl-trichlorosilane, 2-(chloromethyl)allyl-trichlorosilane, (chloromethyl)-phenethyltrichlorosilane, p-(chloromethyl)-phenyltrichlorosilane, chloromethyl-trichlorosilane, chlorophenyltrichlorosilane, 3-chloropropyltrichlorosilane, (3-cyanobutyl)-trichlorosilane, 2-cyanoethyltrichlorosilane, 3-cyanopropyltrichlorosilane, (3-cyclohexenyl)-ethyltrichlorosilane, 3-cyclohexenyl-trichlorosilane, (cyclohexylmethyl)trichlorosilane, cyclohexyl-trichlorosilane, (4-cyclooctenyl)trichlorosilane, cyclooctyltrichlorosilane, cyclopentyltrichlorosilane, n-decyltrichlorosilane, 1,2-dibromoethyl-trichlorosilane, 1,2-dichloroethyltrichlorosilane, (dichloromethyl)-trichlorosilane, dichlorophenyltrichlorosilane, dodecyltrichlorosilane, eicosyltrichlorosilane, docosyltrichlorosilane, ethyltrichlorosilane, (heptadecafluoro-1,1,2,2-tetrahydrodecyl)trichlorosilane, (3-heptafluoro-isopropoxy)propyltrichlorosilane, n-heptyl-trichlorosilane, hexachlorodisilane, hexachlorodisiloxane, n-hexadecyl-trichlorosilane, 5-hexenyltrichlorosilane, hexyltrichlorosilane, isobutyltrichlorosilane, isooctyltrichlorosilane, methacryloyloxypropyl-trichorosilane, 3-(p-methoxyphenyl)propyltrichlorosilane, methyltrichlorosilane, 3,3,4,4,5,5,6,6,6-nonafluorohexyl-trichlorosilane, nonyltrichlorosilane, n-octadecyl-trichlorosilane, 7-octenyl-trichlorosilane, n-octyl-trichlorosilane, pentafluorophenylpropyl-trichlorosilane, pentyltrichlorosilane, phenethyltrichlorosilane, 3-phenoxypropyltrichlorosilane, phenyltrichlorosilane, n-propyltrichlorosilane, p-tolyl-trichlorosilane, trichloromethyltrichlorosilane, (tridecafluoro-1,1,2,2-tetrahydrooctyl)-trichlorosilane, (3,3,3-trifluoropropyl)-trichlorosilane and vinyltrichlorosilane.

The examples of the compound (5) are 1,1,3,3-tetrachloro-1,3-dimethyldisiloxane, 1,1,3,3-tetrachloro-disiloxane and 1,1,3,3-tetrachloro-1,3-diphenyldisiloxane. In the present invention, a plurality of the chlorinated silicon compounds may be selected from the group consisting of tetrachlorosilane and the compound (3) to the compound (5) and used.

Use of the chlorinated silicon compounds given above as the examples makes it possible to produce the PSQ derivatives having various substituents and functional groups. Further, use of the suited compounds among these derivatives makes it possible as well to produce the PSQ derivatives having the other substituents and functional groups according to publicly known methods for introducing substituents and functional groups. It is possible, for example, to synthesize a compound having Si—Cl in a molecule by reacting the PSQ (2) with the chlorinated silicon compound as shown in Example 11 and then introduce other substituents and functional groups making use of this group. When X in Formula (a) or Formula (b) is an aliphatic group having a double bond, a group having halogenated phenyl, hydrogen and halogenated alkyl, it can be utilized for introducing other functional groups. Accordingly, the PSQ (1) having further various functional groups can be synthesized. When X is a functional group or a group having a functional group, the examples of the preferred functional group are —H, —F, —Cl, —Br, —OH, —CF$_3$, perfluoroalkyl, alkoxy, —COOH, 2-oxapropane-1,3-dioyl, polyalkyleneoxy, ester, epoxy, an oxetane ring, —NH$_2$, —CN, —NCO, alkenyl, cycloalkenyl, —SH and —PH$_2$. —H is a functional group bonded directly to Si. —OH, halogen, alkoxy, ester and alkenyl may be bonded directly to an Si atom or may be bonded to an Si atom through a divalent group described later. The other groups excluding —H, —OH, halogen, alkoxy, ester and alkenyl is preferably bonded to an Si atom through a divalent group such as alkylene, alkylcycloalkylene, alkylphenylene or alkylphenylalkylene. The examples of alkenyl are ethenyl and propenyl. The examples of cycloalkenyl are cyclopentadienyl, cyclohexenyl and norbornenyl. The PSQ (1) in which X does not have a functional group can be used as an additive for a polymer.

The specific examples of X in a case where X is a functional group or a group having a functional group shall be shown below.

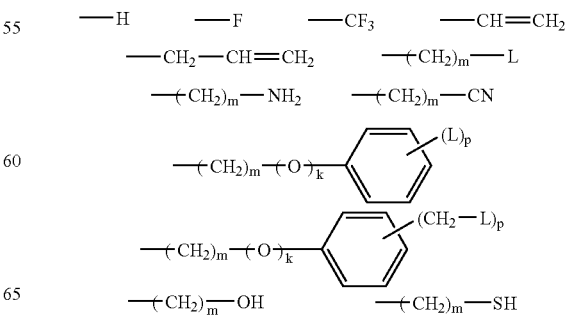

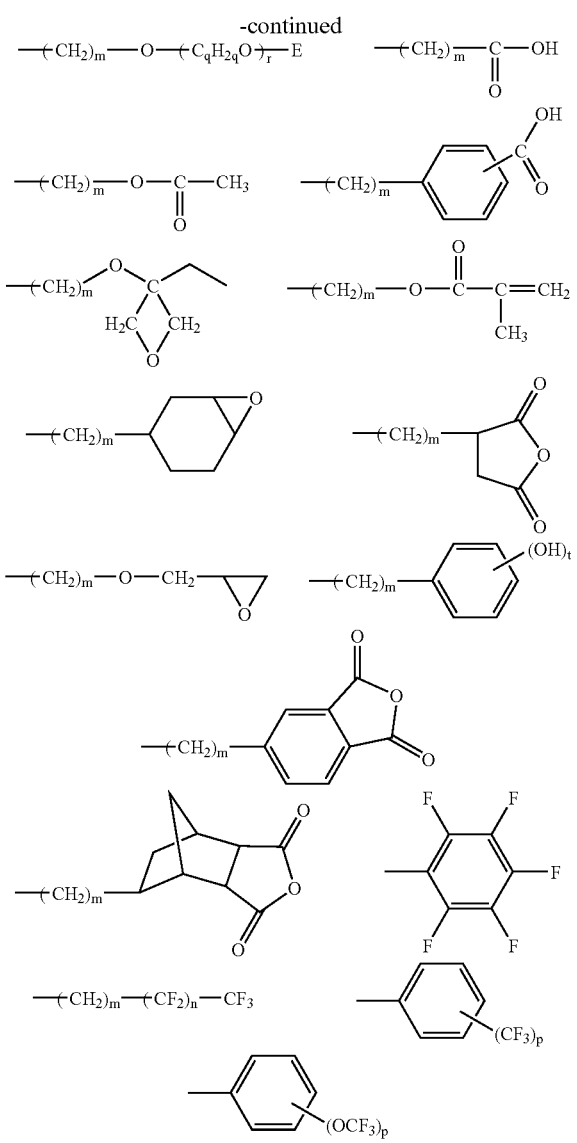

In these formulas, k is 0 or 1; m is an integer of 2 to 4; n is an integer of 0 to 15; L is halogen, and p is an integer of 1 to 5; q is an integer of 2 or 3, and r is an integer of 2 to 200; t is an integer of 1 to 3; and E is hydrogen or alkyl having 1 to 4 carbon atoms. In the examples described above, the bonding positions of —L, —CH$_2$—L, —OH, —COOH, —CF$_3$ and —OCF$_3$ onto a benzene ring are optional respectively. Preferred halogen is F and Cl. The preferred range of r is 2 to 100, and more preferred range is 2 to 20.

A polymer having the PSQ derivative of the present invention as a structural unit can be obtained by using the PSQ (1) having a polymerizable functional group. The PSQ (1) in which X is a group having a polymerizable double bond can be copolymerized with other vinyl base monomers. Applicable polymerization methods are radical polymerization by azo compounds such as azobisisobutyronitrile (AIBN), anionic polymerization by metal alkyl and cationic polymerization by Lewis acids. The PSQ (1) in which X is a group having 2-oxapropane-1,3-dioyl can be used as a raw material for a polycondensed matter. The PSQ (1) which is a group having epoxy or an oxetane ring can also be used as a raw material for a polymer.

Next, a production process for the PSQ (2) shall be explained. The PSQ (2) is obtained by hydrolyzing and condensing the compound (6) in the presence of a monovalent alkaline hydroxide and water:

In Formula (6), R is defined in the same manner as in Formula (2), and A is a hydrolyzable group. Accordingly, the most preferred examples of R are, as described above, phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenyl-ethyl, 4-(1,1-dimethylethyl)phenylethyl, 4-ethenylphenyl-ethyl, 1-(4-ethenylphenyl)ethyl, 4-methoxyphenylpropyl and phenoxypropyl. The preferred examples of A are chlorine and alkoxy. The alkoxy is a group which is separated by hydrolysis, and therefore it is not meaningful so much to restrict the range of the carbon number thereof. A compound having alkoxy having 1 to 4 carbon atoms is advisably used. The compound (6) described above having R and a hydrolyzable group is commercially available, and it can be obtained as well by a conventional synthetic method.

The examples of the compound (6) are phenyl-trichlorosilane, phenyltrimethoxysilane, phenyl-triethoxysilane, phenyltri-n-propoxysilane, phenyltri-n-buthoxysilane, p-tolyltrimethoxysilane, p-tolyl-triethoxysilane, chlorophenyltrichlorosilane, chlorophenyl-trimethoxysilane and chlorophenyl-triethoxysilane.

The examples of the monovalent alkaline oxide are lithium hydroxide, sodium hydroxide, potassium hydroxide and cesium hydroxide. Among them, sodium hydroxide and potassium hydroxide are preferred. A use amount of the monovalent alkaline oxide in the production of the PSQ (2) is 0.3 to 1.5 in terms of a mole ratio to the compound (6). More preferred mole ratio is 0.4 to 0.8. If the mole ratio falls in the above range, a cyclic or linear siloxane compound having a low molecular weight and a siloxane compound having a high molecular weight are prevented from being formed, and the PSQ (2) having a regulated structure is liable to be obtained.

An addition amount of water is 1.0 to 1.5 in terms of a mole ratio to the compound (6). More preferred mole ratio is 1.1 to 1.3. If the mole ratio falls in the above range, remaining of the hydrolyzable group, formation of a siloxane compound having a low molecular weight and formation of a siloxane compound having a structure which is not regulated can be prevented. An addition timing of water shall not specifically be restricted. It may be mixed in advance with the other raw materials or may be added later.

Further, the hydrolytic reaction of the compound (6) is preferably carried out in the presence of an organic solvent. The preferred examples of the organic solvent are alcohols. The preferred examples of the alcohols are linear, branched or cyclic monovalent alcohols. The examples of the linear alcohols are methanol, ethanol, 1-propanol, 1-butanol, 1-pentanol, 1-hexanol, 1-heptanol and 1-octanol. The examples of the branched alcohols are 2-propanol, 2-butanol, 2-methyl-2-propanol, 2-hexanol and 3-hexanol. The examples of the cyclic alcohols are cyclopentanol, cyclohexanol and cycloheptanol. It is estimated that the alcohols contribute to structure regulation in a condensing step.

As described above, it is preferred to use the organic solvent, and a use amount thereof shall not specifically be restricted. Factors for determining a use amount of the organic solvent are economical viewpoints such as an energy efficiency and a time efficiency, and a stirring efficiency attributable to a small solubility of the PSQ (2) in the organic solvent. Accordingly, there is no use range which has to be strictly kept, and considering the factors described above, the standard shall be 0.3 to 50 times in terms of a volume ratio based on the compound (6). More preferred volume ratio shall be 5 to 40 times. It is essential to adopt the optimum conditions in the range of the production conditions described above according to the compound (6) which is used as the raw material.

The PSQ (2) is scarcely soluble in an organic solvent, and therefore it begins to be deposited as the reaction proceeds. Time required for deposition is varied depending on conditions such as the organic solvent used and a use amount thereof, and it is usually several minutes to several ten hours. The PSQ (2) deposited can readily be separated from the solvent by filtration.

The PSQ (2) thus obtained is limited in an analytical method for analyzing the structure thereof because of a low solubility in an organic solvent. Accordingly, monovalent alkaline metal bonded has to be replaced by a trimethylsilyl group by trimethylchlorosilane. A rise in a solubility of the compound in the solvent makes it possible to analyze the structure.

EXAMPLES

The present invention shall more specifically be explained with reference to examples, but the present invention shall not be restricted to these examples. In formulas described in the examples, Ph is phenyl; Me is methyl; TMS is trimethylsilyl; and CN is cyano.

Example 1

<Synthesis-1 of PSQ (2)>

A four neck flask having a content volume of 300 ml equipped with a reflux condenser, a thermometer and a dropping funnel was charged with phenyltrimethoxysilane (24 g), sodium hydroxide (3.2 g), water (2.5 g) and 2-propyl alcohol (120 ml). The flask was sealed with dried nitrogen and heated on an oil bath while stirring by means of a magnetic stirrer until 2-propyl alcohol was refluxed. It was stirred for further 4 hours while refluxing, and then the reaction liquid was left standing still at a room temperature for a night. A deposited precipitate was separated from the reaction liquid by means of a pressure filter equipped with a membrane filter. This was washed once with 2-propyl alcohol. This was dried under reduced pressure at 70° C. for 5 hours to obtain 6.0 g of a white powdery solid matter. This is designated as Compound (2-1).

<Structural Analysis of Compound (2-1)>

A four neck flask having a content volume of 50 ml equipped with a dropping funnel, a reflux condenser and a thermometer was charged with the compound (2-1) (2.3 g), tetrahydrofuran (20 g) and triethylamine (3.2 g), and it was sealed with dried nitrogen. Trimethylchlorosilane (3.4 g) was dropwise added thereto at a room temperature in about one minute while stirring by means of a magnetic stirrer, and the solution was further stirred at a room temperature for 3 hours. Then, water (10 g) was added thereto to dissolve sodium chloride which was a by-product and hydrolyze unreacted trimethylchlorosilane. The resulting reaction mixture was separated to obtain an organic layer. This organic layer was washed once with 1N hydrochloric acid and once with a saturated sodium hydrogencarbonate aqueous solution and further washed repeatedly three times with ion-exchanged water. This organic layer was dried on anhydrous magnesium sulfate and then condensed under reduced pressure by means of a rotary evaporator to obtain a white powdery residue (2.1 g). This is designated as a trimethylsilylated product.

The above trimethylsilylated product was subjected to structural analysis by means of gel permeation chromatography (GPC), $^1$H-NMR, $^{29}$Si-NMR and infrared absorption analysis. In the GPC chart, the above white powdery residue showed a very fine monodispersibility and had a weight average molecular weight (Mw) of 1120 and a number average molecular weight (Mn) of 1080. It was confirmed from the $^1$H-NMR chart that a phenyl group and a trimethylsilyl group were present in an integral ratio of 8:4. Total three peaks of one peak originating in a trimethylsilyl group in −10.6 ppm and two peaks originating in a T structure having a phenyl group in −78.6 ppm and −78.9 ppm in a ratio of 1:1 were confirmed from the $^{29}$Si-NMR chart. The T structure is a structure in which Si is bonded to three O's. Both of $^1$H-NMR and $^{29}$Si-NMR were measured with heavy chloroform used as a solvent and tetramethylsilane used as a standard substance. It was confirmed from the infrared absorption spectrum measured by a KBr tablet method that present were absorptions attributed respectively to harmonic vibration of a substituted benzene ring in 1760 to 1960 cm$^{-1}$, deformation vibration of Si—Ph in 1430 and 1600 cm$^{-1}$, vibration of Si—CH$_3$ in 1250 cm$^{-1}$ and stretching vibration of Si—O—Si in 1130 to 1060 cm$^{-1}$. It was confirmed from the matters described above that the trimethylsilylated product had a structure represented by the following Formula (7). Accordingly, it is judged that the compound (2-1) before trimethylsilylated has a structure represented by the following Formula (8).

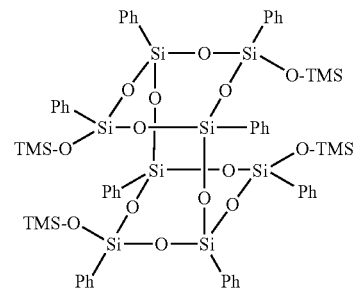

(7)

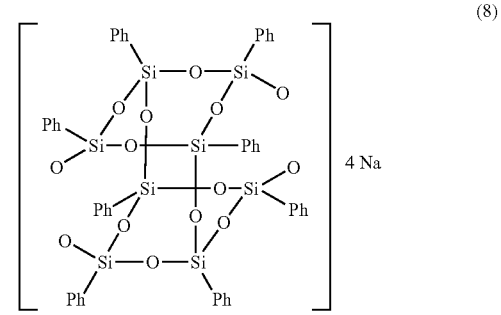

(8)

In the following examples, the PSQ derivative represented by Formula (8) which was produced in the same manner as in Example 1 was designated as the compound (2-1).

Example 2

<Synthesis-2 of PSQ (2)>
Reaction was carried out in the same manner as in Example 1, except that phenyltrimethoxysilane (24 g), sodium hydroxide (3.2 g), water (2.7 g) and 2-propyl alcohol (120 ml) were charged, to obtain 6.2 g of a white powdery solid matter. The white powdery solid matter thus obtained was subjected to structural analysis according to Example 1 to obtain the same results.

Example 3

<Synthesis-3 of PSQ (2)>
Reaction was carried out in the same manner as in Example 1, except that phenyltrimethoxysilane (24 g), sodium hydroxide (3.6 g) and water (2.5 g) were charged, to obtain 5.8 g of a white powdery solid matter. The white powdery solid matter thus obtained was subjected to structural analysis according to Example 1 to obtain the same results.

Example 4

<Synthesis-1 of PSQ (1): Introduction of (Cyanoethyl)Methylsilanediyl>
A three neck flask having a content volume of 300 ml equipped with a dropping funnel, a reflux condenser and a thermometer was charged with the compound (2-1) (11.6 g: 10 mmol), tetrahydrofuran (100 g) and triethylamine (3.0 g: 30 mmol), and it was sealed with dried nitrogen. (Cyanoethyl)methyldichlorosilane (5.0 g: 30 mmol) was dropwise added thereto at a room temperature while stirring by means of a magnetic stirrer. Then, the solution was stirred at a room temperature for one hour. Water (50 g) was added to the reaction liquid to dissolve sodium chloride formed and hydrolyze unreacted (cyanoethyl)methyldichlorosilane. The reaction mixture thus obtained was subjected to liquid separation, and the organic layer was washed once with 1N hydrochloric acid and once with a saturated sodium hydrogencarbonate aqueous solution and further washed repeatedly three times with ion-exchanged water. The organic layer obtained after washing was dried on anhydrous magnesium sulfate and condensed under reduced pressure by means of a rotary evaporator to obtain 7.6 g of a white powdery solid matter.

The above product was subjected to structural analysis by means of GPC, $^1$H-NMR, $^{29}$Si-NMR and a mass spectrum.

It was confirmed from the GPC chart that PSQ (1) was monodispersed and that it had a weight average molecular weight of 920 in terms of polystyrene and a purity of 99%. It was confirmed from the $^1$H-NMR chart that phenyl and methylene in cyanoethyl were present in an integral ratio of 40:4. From the $^{29}$Si-NMR chart, one peak originating in a D structure having (cyanoethyl)methyl was confirmed in −20.83 ppm, and peaks originating in a T structure having a phenyl group were confirmed in −78.16 ppm and −79.27 ppm in a ratio of 1:1. The D structure is a structure in which Si is bonded to two O's. A molecular ion peak of m/z 1259 was confirmed from the mass spectrum. To summarize the matters described above, it is judged that the above compound has a structure represented by the following Formula (9).

$^1$H-NMR (solvent: CDCl$_3$): δ (ppm); 0.38 (s, 6H), 1.08–1.12 (t, 4H), 2.32–2.36 (t, 4H), 7.21–7.50 (m, 40H).
$^{29}$Si-NMR (solvent: CDCl$_3$): δ (ppm); −20.83 (s, 2Si), −78.16 (s, 4Si), −79.27 (t, 4Si).

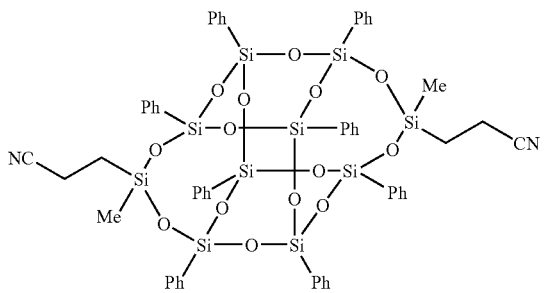

(9)

Example 5

<Synthesis-2 of PSQ (1): Introduction of (3-methacryloyloxypropyl)methylsilanediyl>
Reaction and after-treatment were carried out in the same manner as in Example 4, except that (3-methacryloyloxypropyl)methyldichlorosilane (7.7 g: 30 mmol) was used in place of (cyanoethyl)-methyldichlorosilane. A residue obtained by condensing the reaction liquid under reduced pressure was recrystallized from acetone and dried to obtain 8.4 g of a white powdery solid matter. It is judged from the following analytical data that the above compound has a structure represented by the following Formula (10).

$^1$H-NMR (solvent: CDCl$_3$): δ (ppm); 0.33 (s, 6H), 0.76–0.80 (m, 4H), 1.77–1.84 (m, 10H), 4.00–4.04 (t, 4H), 5.42 (s, 2H), 5.97 (s, 2H), 7.17–7.55 (m, 40H).
$^{29}$Si-NMR (solvent: CDCl$_3$): δ (ppm); −17.88 (s, 2Si), −78.58 (s, 4Si), −79.52 (t, 4Si).

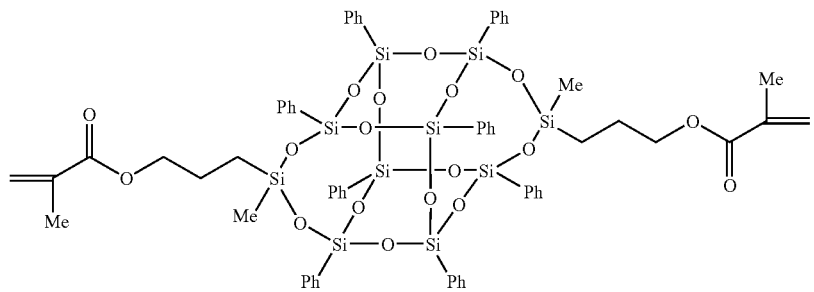

(10)

Example 6

<Synthesis-3 of PSQ (1): Introduction of Methylsilanediyl>

Reaction and after-treatment were carried out in the same manner as in Example 4, except that methyldichlorosilane (3.4 g: 30 mmol) was used in place of (cyanoethyl)methyldichlorosilane. A residue obtained by condensing the reaction liquid under reduced pressure was washed with methanol and dried to obtain 6.9 g of a white powdery solid matter. It is judged from the following analytical data that the above compound has a structure represented by the following Formula (11).

$^1$H-NMR (solvent: CDCl$_3$): δ (ppm); 0.37 (s, 6H), 4.99 (s, 2H), 7.15–7.56 (m, 40H).

$^{29}$Si-NMR (solvent: CDCl$_3$): δ (ppm); −32.78 (s, 2Si), −77.91 (s, 4Si), −79.39 (t, 4Si).

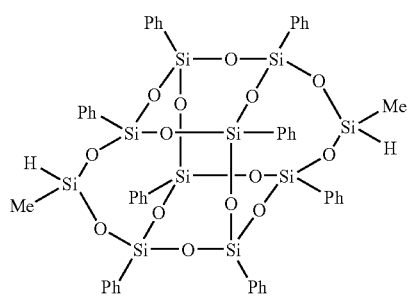

(11)

Example 7

<Synthesis-4 of PSQ (1): Introduction of 3-chloropropylmethylsilanediyl>

Reaction and after-treatment were carried out in the same manner as in Example 4, except that 3-chloropropylmethyldichlorosilane (5.7 g: 30 mmol) was used in place of (cyanoethyl)methyldichlorosilane. A residue obtained by condensing the reaction liquid under reduced pressure was washed with methanol and dried to obtain 7.3 g of a white powdery solid matter. It is judged from the following analytical data that the above compound has a structure represented by the following Formula (12).

$^1$H-NMR (solvent: CDCl$_3$): δ (ppm); 0.30 (s, 6H), 0.81–0.85 (m, 4H), 1.81–1.89 (m, 4H), 3.36–3.40 (t, 4H), 7.18–7.53 (m, 40H).

$^{29}$Si-NMR (solvent: CDCl$_3$): δ (ppm); −18.35 (s, 2Si), −78.61 (s, 4Si), −79.55 (t, 4Si).

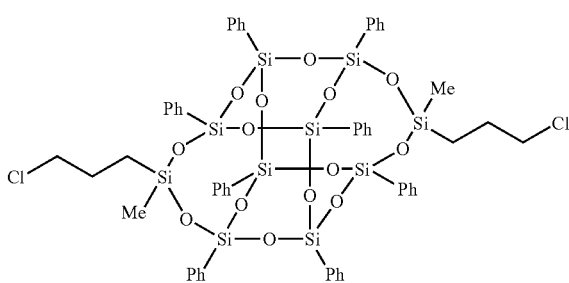

(12)

Example 8

<Synthesis-5 of PSQ (1): Introduction of Methylvinylsilanediyl>

Reaction and after-treatment were carried out in the same manner as in Example 4, except that methylvinyldichlorosilane (4.2 g: 30 mmol) was used in place of (cyanoethyl)methyldichlorosilane. A residue obtained by condensing the reaction liquid under reduced pressure was washed with methanol and dried to obtain 7.2 g of a white powdery solid matter. It is judged from the following analytical data that the above compound has a structure represented by the following Formula (13).

$^1$H-NMR (solvent: CDCl$_3$): δ (ppm); 0.38 (s, 6H), 5.91–6.22 (m, 6H), 7.13–7.53 (m, 40H).

$^{29}$Si-NMR (solvent: CDCl$_3$): δ (ppm); −31.38 (s, 2Si), −78.41 (s, 4Si), −79.57 (s, 4Si).

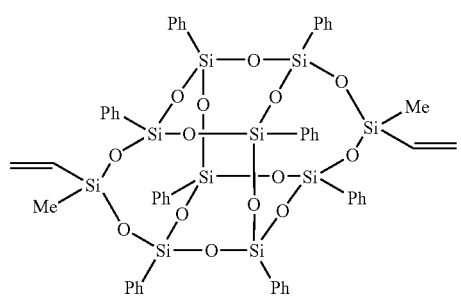

(13)

Example 9

<Synthesis-6 of PSQ (1): Introduction of (3-acryloyloxypropyl)methylsilanediyl>

Reaction and after-treatment were carried out in the same manner as in Example 4, except that the compound (2-1) (8.1 g: 7.04 mmol) obtained in Example 1, triethylamine (1.78 g: 17.6 mmol), tetrahydrofuran (150 g) and (3-acryloyloxypropyl)-methyldichlorosilane (4.0 g: 17.6 mmol) were charged. Impurities were removed from a residue obtained by condensing the reaction liquid under reduced pressure by means of column chromatography (silica gel: 100 g, eluent: toluene/ethyl acetate=9/1), and the residue was recrystallized from ethanol/ethyl acetate to obtain 2.2 g of colorless crystal. It is judged from the following analytical data that the above compound has a structure represented by the following Formula (14).

$^1$H-NMR (solvent: CDCl$_3$): δ(ppm); 0.31 (s, 6H), 0.74–0.78 (t, 4H), 1.74–1.78 (m, 4H), 4.00–4.02 (t, 4H), 5.70 (d, 2H), 5.98 (q, 2H), 6.26–6.29 (d, 2H), 7.17–7.53 (m, 40H).

$^{29}$Si-NMR (solvent: CDCl$_3$): δ (ppm); −18.0 (d, 2Si), −78.6 (s, 4Si), −79.5 (t, 4Si).

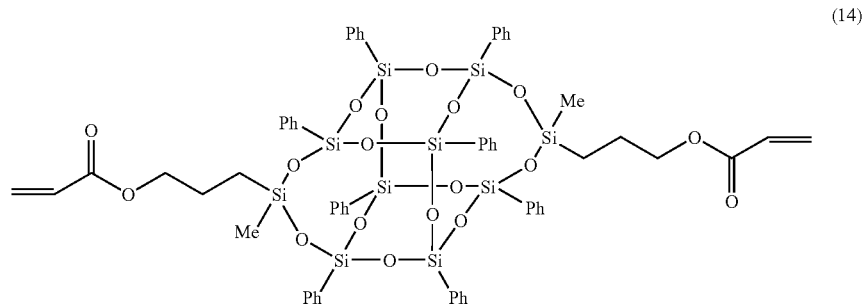

(14)

Example 10

<Synthesis-7 of PSQ (1): Introduction of Acetoxypropylmethylsilanediyl>

Reaction was carried out in the same manner as in Example 4, except that the compound (2-1) (11.6 g: 10 mmol), triethylamine (2.54 g: 25 mmol), tetrahydrofuran (200 g) and 3-acetoxypropylmethyl-dichlorosilane (5.4 g: 25 mmol) were charged and that the reaction time was changed to 3 hours. Toluene (200 ml) and water (100 ml) were added to the reaction liquid and stirred to separate the liquids. The organic layer was washed with water and then dried on anhydrous magnesium sulfate. Toluene was distilled off from the organic layer under reduced pressure, and the low boiling components were removed by heating at 90±5° C. for 30 minutes under a pressure of $3.9 \times 10^{-2}$ MPa. The residue thus obtained was washed with methanol and recrystallized from ethanol/ethyl acetate (100 ml) to obtain 6.51 g of colorless crystal. It is judged from the following analytical data that the above compound has a structure represented by the following Formula (15).

$^1$H-NMR (solvent: CDCl$_3$): δ (ppm); 0.31 (s, 6H), 0.72–0.75 (t, 4H), 1.70–1.74 (m, 4H), 1.88 (s, 6H), 3.91–3.94 (t, 4H), 7.18–7.52 (m, 40H).

$^{29}$SI-NMR (solvent: CDCl$_3$): δ (ppm); −17.8 (d, 2Si), −78.4 (s, 4Si), −79.3 (t, 4Si).

Example 11

<Synthesis-8 of PSQ (1): Introduction of Dichlorosilanediyl>

A three neck flask having a content volume of 300 ml equipped with a dropping funnel, a reflux condenser and a thermometer was charged with the compound (2-1) (11.6 g: 10 mmol) and tetrahydrofuran (100 g), and it was sealed with dried nitrogen. Tetrachlorosilane (68 g: 40 mmol) was dropwise added thereto at a room temperature while stirring by means of a magnetic stirrer. Then, the solution was stirred at a room temperature for 3 hours. Resulting sodium chloride was removed from the reaction mixture by filtering, and unreacted tetrachlorosilane and tetrahydrofuran were removed by condensing under reduced pressure. The residue thus obtained was washed with hexane and dried to obtain 7.6 g of a white powdery solid matter. It is judged from the following analytical data that the above compound has a structure represented by the following Formula (16).

$^{29}$Si-NMR (solvent: CDCl$_3$): δ (ppm); −69.70 (s, 2Si), −76.75 (s, 4Si), −77.50 (s, 4Si).

Mass spectrum (EI: electron impact) m/z 1262

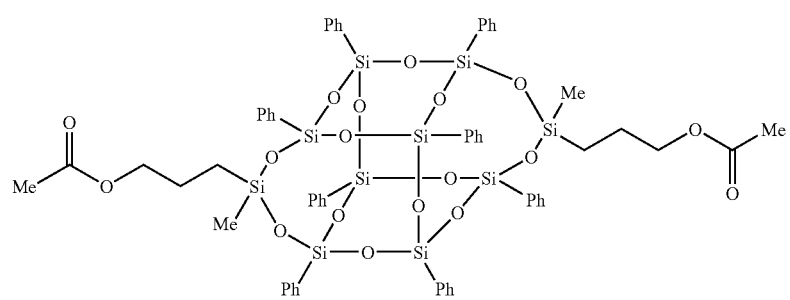

(15)

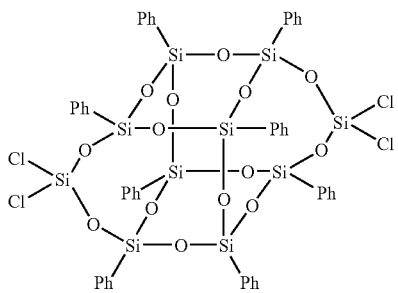

(16)

Example 12

<Synthesis-9 of PSQ (1): Introduction of Methylhydroxysilanediyl>

A three neck flask having a content volume of 300 ml equipped with a dropping funnel, a reflux condenser and a thermometer was charged with the compound (2-1) (11.6 g: 10 mmol), tetrahydrofuran (100 g) and triethylamine (3.0 g: 30 mmol), and it was sealed with dried nitrogen. Methyltrichlorosilane (4.5 g: 30 mmol) was dropwise added thereto at a room temperature while stirring by means of a magnetic stirrer. Then, the solution was stirred at a room temperature for 3 hours. Water (50 g) was added to the reaction liquid to dissolve sodium chloride formed and hydrolyze unreacted methyltrichlorosilane. The reaction mixture thus obtained was subjected to liquid separation, and the organic layer was washed once with 1N hydrochloric acid and once with a saturated sodium hydrogencarbonate aqueous solution and further washed repeatedly three times with ion-exchanged water. The organic layer obtained after washed was dried on anhydrous magnesium sulfate and condensed under reduced pressure by means of a rotary evaporator to obtain 7.1 g of a white powdery solid matter. It is judged from the following analytical data that the above compound has a structure represented by the following Formula (17).

$^{29}$Si-NMR (solvent: CDCl$_3$): δ (ppm); −54.06 (s, 2Si), −78.59 (s, 4Si), −79.17 (s, 4Si).

IR (KBr method): 3450, 3060, 3010, 1590, 1430, 1270, 1130, 1090, 910, 730 cm$^{-1}$.

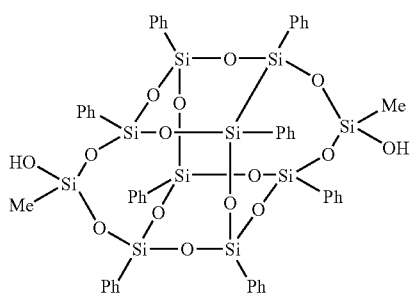

(17)

Example 13

<Synthesis-10 of PSQ (1): Introduction of 1,3-dimethyldisiloxane-1,3-diyl>

Reaction and after-treatment were carried out in the same manner as in Example 4, except that 1,3-dichloro-1,3-dimethyldisiloxane (5.2 g: 30 mmol) was used in place of (cyanoethyl)methyldichlorosilane. A residue obtained by condensing the reaction liquid under reduced pressure was recrystallized from acetone and dried to obtain 7.1 g of a white powdery solid matter. It is judged from the following analytical data that the above compound has a structure represented by the following Formula (18).

$^1$H-NMR (solvent: CDCl$_3$): δ (ppm); 0.19–0.25 (m, 12H), 4.82–4.86 (m, 4H), 7.04–7.46 (m, 40H).

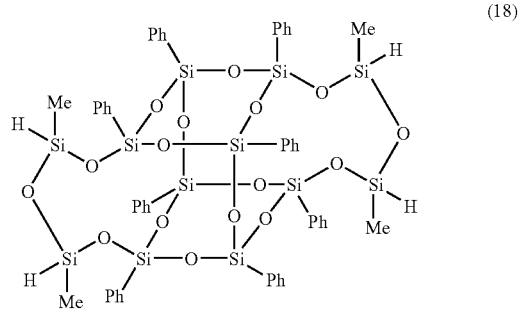

(18)

Example 14

<Synthesis-11 of PSQ (1): Introduction of Glycidyloxypropyl>

A three neck flask having a content volume of 100 ml equipped with a reflux condenser and a thermometer was charged with the compound (11) (10 g: 8.67 mmol) synthesized according to Example 6, toluene (60 g) and allyl glycidyl ether (3.0 g: 26.3 mmol), and it was sealed with dried nitrogen. The solution was heated to 65° C. while stirring by means of a magnetic stirrer, and a Karsted catalyst (a complex of chloroplatinic acid and 1,3-divinyltetramethyldisiloxane; 40 μl) was added thereto through a microsyringe. Thereafter, the mixture was stirred at 65° C. for one hour and then sampled to inspect an infrared absorption spectrum to confirm that an absorption peak (2170 cm$^{-1}$) originating in —H (bonded to Si) disappeared, and thus the reaction was finished. The reaction liquid was condensed under reduced pressure by means of a rotary evaporator to obtain 11.7 g of a white powdery solid matter. It is judged from the following analytical data that the above compound has a structure represented by the following Formula (19).

$^{29}$Si-NMR (solvent: CDCl$_3$): δ (ppm); −17.33 (s, 2Si), −78.67 (s, 4Si), −79.61 (s, 4Si).

$^1$H-NMR (solvent: CDCl$_3$): δ (ppm); 0.30 (s, 6H), 0.72–0.77 (m, 4H), 1.64–1.72 (m, 4H), 2.42–2.66 (m, 4H), 2.95–2.98 (m, 2H), 3.15–3.19 (m, 2H), 3.31–3.37 (m, 4H), 3.43–3.47 (m, 2H), 7.17–7.53 (m, 40H).

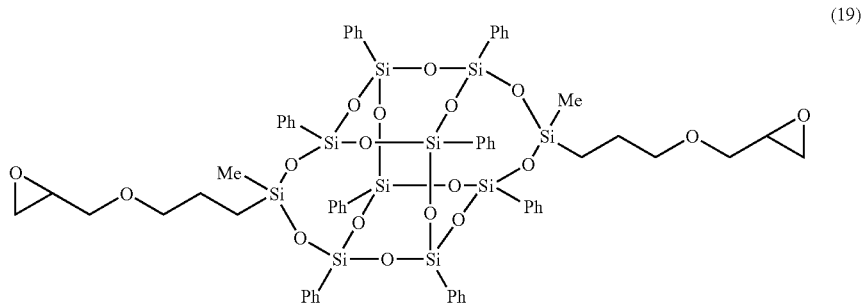

(19)

Example 15

<Synthesis-12 of PSQ (1): Introduction of 2,4-dioxo-3-oxacyclopentylpropyl>

A three neck flask having a content volume of 100 ml equipped with a reflux condenser and a thermometer was charged with the compound (11) (50 g: 43.37 mmol) synthesized according to Example 6, tetrahydrofuran (100 g) and allyl succinate (14.5 g: 103.57 mmol), and it was sealed with dried nitrogen. The solution was heated up to the refluxing temperature while stirring by means of a magnetic stirrer, and then the Karsted catalyst (320 μl) described above was added thereto through a syringe. Thereafter, the mixture was stirred at the refluxing temperature for 7 hours and then sampled to inspect an infrared absorption spectrum to confirm that an absorption peak originating in —H (bonded to Si) disappeared, and thus the reaction was finished. A residue obtained by condensing the reaction liquid under reduced pressure by means of a rotary evaporator was washed with methanol (150 g) to obtain 55.9 g of a white powdery solid matter. It is judged from the following analytical data that the above compound has a structure represented by the following Formula (20).

$^{29}$Si-NMR (solvent: CDCl$_3$): δ (ppm); −18.12 (s, 2Si), −78.55 (s, 4Si), −79.6 (s, 4Si).

$^1$H-NMR (solvent: CDCl$_3$): δ (ppm); 0.32 (s, 6H), 0.70–0.79 (m, 4H), 1.32–1.42 (m, 6H), 1.73–1.79 (m, 2H), 1.88–1.99 (m, 2H), 2.23–2.36 (m, 2H), 2.50–2.60 (m, 2H), 7.14–7.58 (m, 40H).

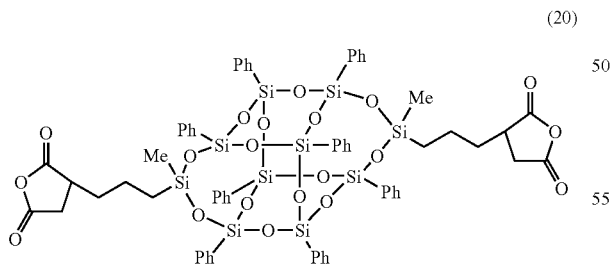

(20)

INDUSTRIAL APPLICABILITY

The PSQ derivative of the present invention represented by Formula (1) can usefully be used as an electronic material, an optical material, an electronic-optical material, a catalyst carrier and a monomer. Further, the above PSQ derivative can also usefully be used as an additive for raising a fire retardancy, a heat resistance, a weatherability, an electrical insulating property, a surface characteristic, a hardness, a dynamic strength and a chemical resistance of a polymer material. Use of the PSQ derivative of the present invention represented by Formula (2) as a starting material makes it possible to readily introduce a plurality of functional groups and other groups selected according to the purposes into the PSQ skeleton. Also, suited selection of the groups to be introduced makes it possible to produce the PSQ derivative which is improved in a compatibility with resins. Further, when two functional groups are introduced, obtained is the PSQ derivative in which the respective functional groups are introduced into opposite positions with the PSQ skeleton set as the center. This is the PSQ derivative represented by Formula (1). A process for readily synthesizing the compound having functional groups in opposite positions with the PSQ skeleton set as the center has been provided by the present invention. The present invention makes it easy to introduce the completely condensed type PSQ derivative into a principal chain of a high molecular compound.

The invention claimed is:

1. A silsesquioxane derivative represented by Formula (1):

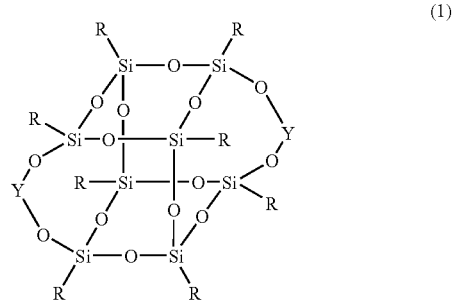

(1)

wherein each R is alkyl having 1 to 45 carbon atoms, a substituted or non-substituted aryl, or a substituted or non-substituted arylalkyl; Y is a group represented by Formula (a) or Formula (b); in the alkyl having 1 to 45 carbon atoms, optional hydrogen may be replaced by fluorine, and optional —CH$_2$— may be replaced by —O—, —CH=CH—, cycloalkylene or cycloalkenylene; in alkylene of the substituted or non-substituted arylalkyl, optional hydrogen may be replaced by fluorine, and optional —CH$_2$— may be replaced by —O—, —CH=CH— or cycloalkylene:

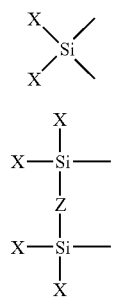

wherein in Formula (a), each X is independently alkyl having 1 to 45 carbon atoms, a substituted or non-substituted phenyl, or a group having a functional group, and at least one X is a group having a functional group; in Formula (b), each X is independently hydrogen, alkyl having 1 to 45 carbon atoms, a substituted or non-substituted phenyl, or a group having a functional group, Z is —O—, —CH$_2$— or a single bond, and at least one X is hydrogen or a group having a functional group; in the alkyl having 1 to 45 carbon atoms, optional hydrogen may be replaced by fluorine, and optional —CH$_2$— may be replaced by —O—, —CH=CH—, cycloalkylene or cycloalkenylene; the group having a functional group in Formula (a) is cyanoalkyl, carboxyalkyl, mercaptoalkyl, acryloyloxyalkyl, methacryloyloxyalkyl, glycidyloxyalkyl, 2,4-dioxo-3-oxa-cyclopentylalkyl, or oxetanyloxyalkyl, and the carbon number of alkylene in these groups is 2 to 4; the group having a functional group in Formula (b) is chloroalkyl, cyanoalkyl, aminoalkyl, hydroxyalkyl, carboxyalkyl, mercaptoalkyl, ethenyl, 2-propenyl, acryloyloxyalkyl, methacryloyloxyalkyl, acetoxyalkyl, glycidyloxyalkyl, 2,4-dioxo-3-oxa-cyclopentylalkyl, or oxetanyloxyalkyl, and the carbon number of alkylene in these groups is 2 to 4; and, when two Xs in Formula (a) are same groups, they may be chlorines.

2. The silsesquioxane derivative according to claim 1, wherein each R is independently a substituted or non-substituted phenyl; in the substituted phenyl, at least one hydrogen of phenyl is replaced by halogen or alkyl having 1 to 10 carbon atoms; in the above alkyl having 1 to 10 carbon atoms, optional hydrogen may be replaced by fluorine, and optional —CH$_2$— may be replaced by —O—, —CH=CH—, cycloalkylene or phenylene; and, when the phenyl has plural substituents, the substituents may be the same group or different groups.

3. The silsesquioxane derivative according to claim 1, wherein each R is independently a substituted or non-substituted phenylalkyl; in the substituted phenylalkyl, at least one hydrogen of phenyl is replaced by halogen or alkyl having 1 to 12 carbon atoms; in the above alkyl having 1 to 12 carbon atoms, optional hydrogen may be replaced by fluorine, and optional —CH$_2$— may be replaced by —O—, —CH=CH—, cycloalkylene or phenylene; in alkylene of the substituted or non-substituted phenylalkyl, the number of carbon atoms is 1 to 12, optional hydrogen may be replaced by fluorine, and optional —CH$_2$— may be replaced by —O— or cycloalkylene; and, when the phenyl has plural substituents, the substituents may be the same group or different groups.

4. The silsesquioxane derivative according to claim 1, wherein each R is independently alkyl having 1 to 8 carbon atoms, a substituted or non-substituted phenyl, or a substituted or non-substituted phenylalkyl; in the alkyl having 1 to 8 carbon atoms, optional hydrogen may be replaced by fluorine, and optional —CH$_2$—may be replaced by —O—, —CH=CH—, cycloalkylene or cycloalkenylene; in the substituted phenyl, at least one hydrogen of phenyl is replaced by halogen, methyl or methoxy; in the substituted phenylalkyl, at least one hydrogen of phenyl is replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; and, when the phenyl has plural substituents, the substituents may be the same group or different groups.

5. The silsesquioxane derivative according to claim 1, wherein all of R's are the same group selected from alkyl having 1 to 8 carbon atoms, a substituted or non-substituted phenyl, or a substituted or non-substituted phenylalkyl; in the alkyl having 1 to 8 carbon atoms, optional hydrogen may be replaced by fluorine, and optional —CH$_2$— may be replaced by —O—, —CH=CH—, cycloalkylene or cycloalkenylene; in the substituted phenyl, at least one hydrogen of phenyl is replaced by halogen, methyl or methoxy; in the substituted phenylalkyl, at least one hydrogen of phenyl is replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; and, when the phenyl has plural substituents, the substituents may be the same group or different groups.

6. The silsesquioxane derivative according to claim 1, wherein all of R's are the same group selected from a substituted or non-substituted phenyl and a substituted or non-substituted phenylalkyl; in the substituted phenyl, at least one hydrogen of phenyl is replaced by halogen, methyl or methoxy; in the substituted phenylalkyl, at least one hydrogen of phenyl is replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; and, when the phenyl has plural substituents, the substituents may be the same group or different groups.

7. The silsesquioxane derivative according to claim 1, wherein all of R's are non-substituted phenyls.

8. The silsesquioxane derivative according to claim 1, wherein at least one X in each of Formula (a) and Formula (b) is a polymerizable group.

9. The silsesquioxane derivative according to claim 1, wherein at least one X in Formula (a) acryloyloxyalkyl, methacryloyloxyalkyl, glycidyloxyalkyl, or oxetanyloxyalkyl, and at least one X in Formula (b) is ethenyl, 2-propenyl, acryloyloxyalkyl, methacryloyloxyalkyl, glycidyloxyalkyl or oxetanyloxyalkyl.

10. The silsesquioxane derivative according to claim 1, wherein at least one X in each of Formula (a) and Formula (b) is 2,4-dioxo-3-oxa-cyclopentylalkyl.

11. A polymer having the silsesquioxane derivative defined in claim 8 as a structural unit, obtained by polymerizing the silsesquioxane derivative defined in claim 8 as a monomer, a comonomer, or a raw material for a polycondensed matter.

12. A polymer having the silsesquioxane derivative defined in claim 9 as a structural unit, obtained by polymerizing the silsesquioxane derivative defined in claim 9 as a monomer or comonomer.

13. A polymer having the silsesquioxane derivative defined in claim 10 as a structural unit, obtained by polymerizing the silsesquioxane derivative defined in claim 10 as a raw material for a polycondensed matter.

14. A production process for the silsesquioxane derivative represented by Formula (1), characterized by reacting a silsesquioxane derivative represented by Formula (2) with a silicon compound having at least two chlorines:

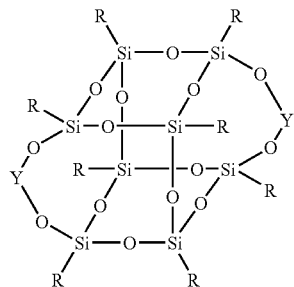
(1)

wherein each R is a group independently selected from hydrogen, the group of alkyls having 1 to 45 carbon atoms, the group of substituted or non-substituted aryls and the group of substituted or non-substituted arylalkyls; Y is a group represented by Formula (a) or Formula (b); in the alkyl having 1 to 45 carbon atoms, optional hydrogen may be replaced by fluorine, and optional —CH$_2$— may be replaced by —O—, —CH=CH—, cycloalkylene or cycloalkenylene; in alkylene of the substituted or non-substituted arylalkyl, optional hydrogen may be replaced by fluorine, and optional —CH$_2$— may be replaced by —O—, —CH=CH— or cycloalkylene:

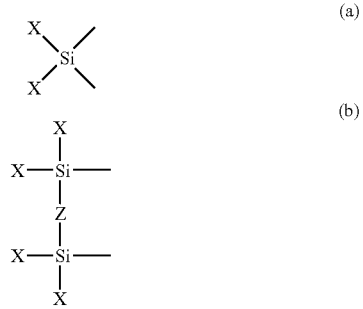
(a)
(b)

wherein each X is independently hydrogen, halogen, a hydroxyl group, alkyl having 1 to 45 carbon atoms, a substituted or non-substituted aryl, a substituted or non-substituted arylalkyl, a functional group or a group having a functional group; in the alkyl having 1 to 45 carbon atoms, optional hydrogen may be replaced by fluorine, and optional —CH$_2$—may be replaced by —O—, —CH=CH—, cycloalkylene or cycloalkenylene; in alkylene of the substituted or non-substituted arylalkyl, optional hydrogen may be replaced by fluorine, and optional —CH$_2$— may be replaced by —O—, —CH=CH— or cycloalkylene; and, Z is —O—, —CH$_2$— or a single bond:

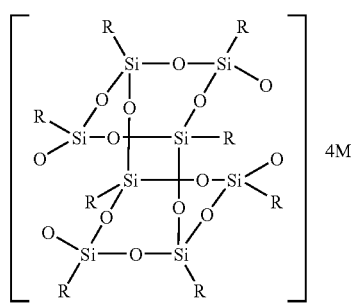
(2)

wherein R is the same as R in Formula (1); and, M is a monovalent alkaline metal atom.

15. The production process according to claim 14, wherein the silicon compound having at least two chlorines is a compound represented by Formula (3):

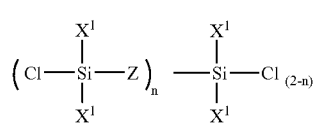
(3)

wherein n is 0 or 1; Z and $X^1$ are defined in the same manner as Z and X in Formula (b) respectively.

16. The production process according to claim 14, wherein the silicon compound having at least two chlorines is a compound represented by Formula (4):

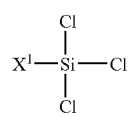
(4)

wherein $X^1$ is defined in the same manner as X in Formula (a).

17. The production process according to claim 14, wherein the silicon compound having at least two chlorines is a compound represented by Formula (5):

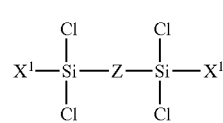
(5)

wherein Z and $X^1$ are defined in the same manner as Z and X in Formula (b) respectively.

18. A silsesquioxane derivative represented by Formula (2):

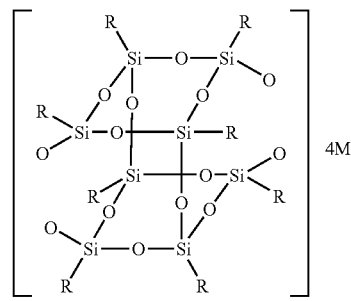
(2)

wherein each R is a group independently selected from hydrogen, the group of alkyls having 1 to 45 carbon atoms, the group of substituted or non-substituted aryls and the group of substituted or non-substituted arylalkyls; in the alkyl having 1 to 45 carbon atoms, optional hydrogen may be replaced by fluorine, and optional —CH$_2$— may be replaced by —O—, —CH=CH—, cycloalkylene or cycloalkenylene; in alkylene of the substituted or non-substituted arylalkyl, optional hydrogen may be replaced by fluorine, and optional —CH$_2$— may be replaced by —O—, —CH=CH— or cycloalkylene; and, M is a monovalent alkaline metal atom.

19. The silsesquioxane derivative according to claim 18, wherein all of R's are the same group selected from alkyl having 1 to 8 carbon atoms, a substituted or non-substituted phenyl, a substituted or non-substituted phenylalkyl, and naphthyl; in the alkyl having 1 to 8 carbon atoms, optional hydrogen may be replaced by fluorine, and optional —CH$_2$— may be replaced by —O—, —CH=CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; and, when the phenyl has plural substituents, the substituents may be the same group or different groups.

20. A production process for the silsesquioxane derivative represented by Formula (2), which comprises hydrolyzing and condensing a silicon compound represented by Formula (6) in the presence of a monovalent alkaline metal hydroxide, water and an alcohol:

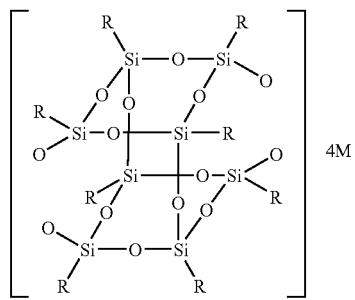

wherein each R is a group independently selected from hydrogen, the group of alkyls having 1 to 45 carbon atoms, the group of substituted or non-substituted aryls and the group of substituted or non-substituted arylalkyls; in the alkyl having 1 to 45 carbon atoms, optional hydrogen may be replaced by fluorine, and optional —CH$_2$— may be replaced by —O—, —CH=CH—, cycloalkylene or cycloalkenylene; in alkylene of the substituted or non-substituted arylalkyl, optional hydrogen may be replaced by fluorine, and optional —CH$_2$— may be replaced by —O—, —CH=CH— or cycloalkylene; and, M is a monovalent alkaline metal atom:

wherein R is the same as R in Formula (2); and, A is a hydrolyzable group.

21. The production process according to claim 20, wherein the monovalent alkaline metal hydroxide is sodium hydroxide or potassium hydroxide.

22. The production process according to claim 20, wherein A is chlorine or alkyloxy having 1 to 4 carbon atoms.

23. The production process according to claim 20, wherein all of R's in formula (2) are the same group selected from alkyl having 1 to 8 carbon atoms, a substituted or non-substituted phenyl, a substituted or non-substituted phenylalkyl, and naphthyl; in the alkyl having 1 to 8 carbon atoms, optional hydrogen may be replaced by fluorine, and optional —CH$_2$— may be replaced by —O—, —CH=CH—, cycloalkylene or cycloalkenylene; in the substituted or non-substituted phenyl, optional hydrogen on the benzene ring may be replaced by halogen, methyl or methoxy; in phenyl of the substituted or non-substituted phenylalkyl, optional hydrogen on the benzene ring may be replaced by fluorine, alkyl having 1 to 4 carbon atoms, ethenyl or methoxy; in alkylene of the substituted or non-substituted phenylalkyl, the number of carbon atoms is 1 to 8, and optional —CH$_2$— may be replaced by —O—, —CH=CH— or cycloalkylene; and, when the phenyl has plural substituents, the substituents may be the same group or different groups; and, A is chlorine or alkyloxy having 1 to 4 carbon atoms.

* * * * *